US010226549B2

(12) United States Patent
Chun et al.

(10) Patent No.: US 10,226,549 B2
(45) Date of Patent: Mar. 12, 2019

(54) THERMOSENSITIVE BIODEGRADABLE HYDROGEL

(71) Applicant: THE CATHOLIC UNIVERSITY OF KOREA INDUSTRY-ACADEMIC COOPERATION FOUNDATION, Seoul (KR)

(72) Inventors: Heung Jae Chun, Seoul (KR); Dae Hyeok Yang, Seoul (KR); Su Jung You, Seoul (KR); Hyun Joo Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/449,464

(22) Filed: Mar. 3, 2017

(65) Prior Publication Data

US 2017/0197012 A1    Jul. 13, 2017

Related U.S. Application Data

(63) Continuation-in-part of application No. PCT/KR2015/009024, filed on Aug. 28, 2015.

(30) Foreign Application Priority Data

Sep. 4, 2014   (KR) .................. 10-2014-0117892

(51) Int. Cl.
| | |
|---|---|
| *A61L 27/14* | (2006.01) |
| *A61L 27/22* | (2006.01) |
| *A61L 27/52* | (2006.01) |
| *A61L 27/56* | (2006.01) |
| *A61L 27/18* | (2006.01) |
| *A61L 27/38* | (2006.01) |
| *A61L 27/50* | (2006.01) |
| *A61L 27/54* | (2006.01) |
| *A61L 27/58* | (2006.01) |

(52) U.S. Cl.
CPC .............. *A61L 27/52* (2013.01); *A61L 27/14* (2013.01); *A61L 27/18* (2013.01); *A61L 27/22* (2013.01); *A61L 27/38* (2013.01); *A61L 27/50* (2013.01); *A61L 27/54* (2013.01); *A61L 27/56* (2013.01); *A61L 27/58* (2013.01); *A61L 2300/25* (2013.01)

(58) Field of Classification Search
None
See application file for complete search history.

(56) References Cited

U.S. PATENT DOCUMENTS

2010/0098762 A1   4/2010   Han et al.
2012/0177740 A1   7/2012   Kim et al.

FOREIGN PATENT DOCUMENTS

| CN | 102604065 B | * | 9/2013 |
|---|---|---|---|
| KR | 10-2006-0098548 A | | 9/2006 |
| KR | 10-0687281 B1 | | 2/2007 |
| KR | 10-1001855 B1 | | 12/2010 |
| KR | 10-2012-0081890 A | | 7/2012 |
| KR | 10-2013-0091818 A | | 8/2013 |

OTHER PUBLICATIONS

Gao et al., Mol. Pharmaceutics, 11, pp. 1042-1052. (Year: 2014).*
Delaittre et al., Soft Matter, 8, pp. 7323-7347. (Year: 2012).*
Liechty et al., Annu Rev Chem Biomol Eng, 1, pp. 149-173. (Year: 2010).*
Scherlund et al., Thermosetting microemulsions and mixed micellar solutions as drug delivery systems for periodontal anesthesia, International Journal of Pharmaceutics, vol. 194, pp. 103-116, (2000).
Harmon et al., Photo-Cross-Linkable PNIPAAm Copolymers. 2. Effects of Constraint on Temperature and pH-Responsive Hydrogel Layers, Macromolecules, vol. 36, pp. 162-172, (2003).
Jeong et al., In situ gelation of PEG-PLGA-PEG triblock copolymer aqueous solutions and degradation thereof, J. Biomed. Mater. Res., vol. 50, No. 2, pp. 171-177, (2000).
Zhao et al., Synthesis and Properties of PCL-PEG-PCL Block Copolymer, Journal of Functional Polymers, vol. 15, No. 1, 4 pages, (2002).
Ogiso et al., Comparative push-out test of dense HA implants and HA-coated implants: Findings in a canine study, J. Biomed. Mater. Res., vol. 39, No. 3, pp. 364-372, (1998).

* cited by examiner

*Primary Examiner* — Abigail Vanhorn
(74) *Attorney, Agent, or Firm* — Vorys, Sater, Seymour & Pease LLP; Mih Suhn Koh

(57) ABSTRACT

There is provided a thermosensitive biodegradable hydrogel including MPEG-PCL to which a cell-adhesive peptide binds, and MPEG-PCL. The thermosensitive biodegradable hydrogel has excellent cellular adhesiveness while maintaining thermosensitivity of polymers intact, and is biodegradable in vivo after a predetermined period of time.

5 Claims, 19 Drawing Sheets

Specification includes a Sequence Listing.

(A)

(B)

(C)

(D)

SEQUENCE LISTING

```
<160> NUMBER OF SEQ ID NOS: 21

<210> SEQ ID NO 1
<211> LENGTH: 3
<212> TYPE: PRT
<213> ORGANISM: Artificial Sequence
<220> FEATURE:
<223> OTHER INFORMATION: cell-adhesive peptide (RGD)

<400> SEQUENCE: 1

Arg Gly Asp
  1

<210> SEQ ID NO 2
<211> LENGTH: 4
<212> TYPE: PRT
<213> ORGANISM: Artificial Sequence
<220> FEATURE:
<223> OTHER INFORMATION: cell-adhesive peptide (REDV)

<400> SEQUENCE: 2

Arg Glu Asp Val
  1

<210> SEQ ID NO 3
<211> LENGTH: 3
<212> TYPE: PRT
<213> ORGANISM: Artificial Sequence
<220> FEATURE:
<223> OTHER INFORMATION: cell-adhesive peptide (LDV)

<400> SEQUENCE: 3

Leu Asp Val
  1

<210> SEQ ID NO 4
<211> LENGTH: 5
<212> TYPE: PRT
<213> ORGANISM: Artificial Sequence
<220> FEATURE:
<223> OTHER INFORMATION: cell-adhesive peptide (YIGSR)
```

```
<400> SEQUENCE: 4

Tyr Ile Gly Ser Arg
 1               5

<210> SEQ ID NO 5
<211> LENGTH: 5
<212> TYPE: PRT
<213> ORGANISM: Artificial Sequence
<220> FEATURE:
<223> OTHER INFORMATION: cell-adhesive peptide (PDSGR)

<400> SEQUENCE: 5

Pro Asp Ser Gly Arg
 1               5

<210> SEQ ID NO 6
<211> LENGTH: 5
<212> TYPE: PRT
<213> ORGANISM: Artificial Sequence
<220> FEATURE:
<223> OTHER INFORMATION: cell-adhesive peptide (IKVAV)

<400> SEQUENCE: 6

Ile Lys Val Ala Val
 1               5

<210> SEQ ID NO 7
<211> LENGTH: 10
<212> TYPE: PRT
<213> ORGANISM: Artificial Sequence
<220> FEATURE:
<223> OTHER INFORMATION: cell-adhesive peptide (RNIAEIIKDA)

<400> SEQUENCE: 7

Arg Asn Ile Ala Glu Ile Ile Lys Asp Ala
 1               5                  10

<210> SEQ ID NO 8
<211> LENGTH: 20
<212> TYPE: DNA
<213> ORGANISM: Artificial Sequence
<220> FEATURE:
<223> OTHER INFORMATION: forward primer for GAPDH

<400> SEQUENCE: 8
ggaatccact ggcgtcttca                                         20

<210> SEQ ID NO 9
<211> LENGTH: 20
<212> TYPE: DNA
<213> ORGANISM: Artificial Sequence
<220> FEATURE:
<223> OTHER INFORMATION: reverse primer for GAPDH

<400> SEQUENCE: 9
tacttctcgt ggttcacgcc                                         20

<210> SEQ ID NO 10
<211> LENGTH: 20
<212> TYPE: DNA
<213> ORGANISM: Artificial Sequence
<220> FEATURE:
<223> OTHER INFORMATION: forward primer for ITGA2

<400> SEQUENCE: 10
```

```
tgctgctgta cacctgatgg                                              20

<210> SEQ ID NO 11
<211> LENGTH: 20
<212> TYPE: DNA
<213> ORGANISM: Artificial Sequence
<220> FEATURE:
<223> OTHER INFORMATION: reverse primer for ITGA2

<400> SEQUENCE: 11
tgtaccccac cccacataca                                              20

<210> SEQ ID NO 12
<211> LENGTH: 20
<212> TYPE: DNA
<213> ORGANISM: Artificial Sequence
<220> FEATURE:
<223> OTHER INFORMATION: forward primer for ITGA5

<400> SEQUENCE: 12
ctccttcttc ggcttctcgg                                              20

<210> SEQ ID NO 13
<211> LENGTH: 20
<212> TYPE: DNA
<213> ORGANISM: Artificial Sequence
<220> FEATURE:
<223> OTHER INFORMATION: reverse primer for ITGA5

<400> SEQUENCE: 13
gcccagggac agaagtagac                                              20

<210> SEQ ID NO 14
<211> LENGTH: 20
<212> TYPE: DNA
<213> ORGANISM: Artificial Sequence
<220> FEATURE:
<223> OTHER INFORMATION: forward primer for ITGB1

<400> SEQUENCE: 14
tcaagagtct cgggacggat                                              20

<210> SEQ ID NO 15
<211> LENGTH: 20
<212> TYPE: DNA
<213> ORGANISM: Artificial Sequence
<220> FEATURE:
<223> OTHER INFORMATION: reverse primer for ITGB1

<400> SEQUENCE: 15
ctcactcgtg caagggttct                                              20

<210> SEQ ID NO 16
<211> LENGTH: 20
<212> TYPE: DNA
<213> ORGANISM: Artificial Sequence
<220> FEATURE:
<223> OTHER INFORMATION: forward primer for Runx-2

<400> SEQUENCE: 16
ctcagccatt ctgaagccca                                              20

<210> SEQ ID NO 17
<211> LENGTH: 20
<212> TYPE: DNA
<213> ORGANISM: Artificial Sequence
```

```
<220> FEATURE:
<223> OTHER INFORMATION: reverse primer for Runx-2

<400> SEQUENCE: 17
cccctcgatt gttatcggca                                               20

<210> SEQ ID NO 18
<211> LENGTH: 20
<212> TYPE: DNA
<213> ORGANISM: Artificial Sequence
<220> FEATURE:
<223> OTHER INFORMATION: forward primer for COL1

<400> SEQUENCE: 18
gcgtccgatc tgtgaagaca                                               20

<210> SEQ ID NO 19
<211> LENGTH: 20
<212> TYPE: DNA
<213> ORGANISM: Artificial Sequence
<220> FEATURE:
<223> OTHER INFORMATION: reverse primer for COL1

<400> SEQUENCE: 19
ctcctgtggt ttcctggtcc                                               20

<210> SEQ ID NO 20
<211> LENGTH: 20
<212> TYPE: DNA
<213> ORGANISM: Artificial Sequence
<220> FEATURE:
<223> OTHER INFORMATION: forward primer for Osteocalcin

<400> SEQUENCE: 20
cttcgtgtcc aagagggagg                                               20

<210> SEQ ID NO 21
<211> LENGTH: 19
<212> TYPE: DNA
<213> ORGANISM: Artificial Sequence
<220> FEATURE:
<223> OTHER INFORMATION: reverse primer for Osteocalcin

<400> SEQUENCE: 21
ctccagggga tccgggtaa                                                19
```

THERMOSENSITIVE BIODEGRADABLE HYDROGEL

CROSS-REFERENCE TO RELATED APPLICATION

This application claims priority to and the benefit of Korean Patent Application No. 2014-0117892, filed on Sep. 4, 2014, the disclosure of which is incorporated herein by reference in its entirety.

SEQUENCE LISTING

The Sequence Listing submitted in text format (.txt) filed on Mar. 3, 2017, named "SequenceListing.txt", created on Mar. 2, 2017, 4.41 KB), is incorporated herein by reference.

BACKGROUND

1. Field of the Invention

The present invention relates to a thermosensitive biodegradable hydrogel, and more particularly, to a thermosensitive biodegradable hydrogel including methoxy polyethylene glycol-polycaprolactone (MPEG-PCL) to which a cell-adhesive peptide binds, and methoxy polyethylene glycol-polycaprolactone (MPEG-PCL).

2. Discussion of Related Art

As one new field that has emerged with the development of science, tissue engineering is a multidisciplinary science which involves an integrated application of fundamental concepts and scientific techniques from various fields of sciences such as life science, engineering, medical science, and the like, and an applied science which aims to understand the relationship between the structure and function of a biological tissue and also synthesize an artificial tissue which may be transplanted into the body in order to replace a damaged tissue or organ with a normal tissue or regenerate the damaged tissue or organ, thereby maintaining, improving or restoring the function of a human body.

Two representative tissue engineering techniques using hydrogel are summarized, as follows. One technique includes removing a desired tissue from a patient body, isolating cells from the removed tissue, proliferating the isolated cells through the cell culture until an amount of the cells reaches a desired amount, and mixing the proliferated cells with transplantable hydrogels to immediately transplant the resulting mixture into the human body, or culturing the cells in vitro in hydrogel for a certain period of time to transplant the obtained hydrogel cultures into the human body. According to this technique, the hydrogel transplanted in a sol state is converted into a gel state in vivo in the condition of the body temperature, and blood vessels are newly formed around the hydrogel while oxygen and nutrients are being supplied to cells due to the diffusion of bodily fluids. In this case, when blood is supplied, the cells are grown and divided to form a new tissue and organ. After a predetermined period of time, the hydrogel is released into the body or degraded, and eventually disappears.

The other technique is a method that includes mixing a certain drug with hydrogel to transplant the resulting mixture into the human body. In a transplanted site, the hydrogel in a sol state is converted into a gel state due to the body temperature. In this case, the drub is released at a proper concentration for a long time while the hydrogel is being slowly degraded.

Therefore, for such a tissue engineering study, it is, first of all, important to prepare a thermosensitive hydrogel similar to a biological tissue and may be converted into a gel state at or near the body temperature. Hydrogel used for regeneration of human tissues is maintained in a sol state near room temperature, but may be converted into a gel state near the body temperature. In this case, the cells should have cell affinity to form a tissue with a three-dimensional structure in the hydrogel, and play a role as an intermediate barrier positioned between the transplanted cells and host cells.

Examples of the representative hydrogels having such characteristics such as thermosensitivity include Pluronic (P. Holmqvist et al., Int. J. Pharm. 194: 103, 2000), poly-N-isopropylacrylamide (PNIPAAm) (M. Harmon et al., Macromolecules 36: 1, 2003), hyaluronic acid (HA) (M. Ogiso et al., J. Biomed. Mater. Res. 39: 3, 1998), linear polyethylene glycol (PEG)-poly(lactic-co-glycolic acid) copolymer (PLGA)-polyethylene glycol (PEG) (B. Jeong et al., J. Biomed. Mater. Res. 50: 2, 2000), linear polyethylene glycol (PEG)-poly(lactic acid) (PLA)-polyethylene glycol (PEG), star-shaped poly(lactic acid) (PLA)-polyethylene glycol (PEG), star-shaped poly-ε-caprolactone (PCL)-polyethylene glycol (PEG) (S. Zhao et al., J. Func. Polym. 15: 1, 2002), etc. However, the hydrogels listed above have drawbacks in that they relatively low mechanical properties, and have no sufficient cell affinity to be used for tissue regeneration.

SUMMARY OF THE INVENTION

Therefore, the present invention is designed to solve the problems of the prior art, and it is an object of the present invention to provide a thermosensitive biodegradable hydrogel which has excellent cellular adhesiveness while maintaining thermosensitivity of polymers intact, and is biodegradable in vivo after a predetermined period of time.

According to an aspect of the present invention, there is provided a thermosensitive biodegradable hydrogel which includes a methoxy polyethylene glycol-polycaprolactone (MPEG-PCL) copolymer, to which a cell-adhesive peptide binds, represented by the following Formula 1, and a methoxy polyethylene glycol-polycaprolactone (MPEG-PCL) copolymer represented by the following Formula 2:

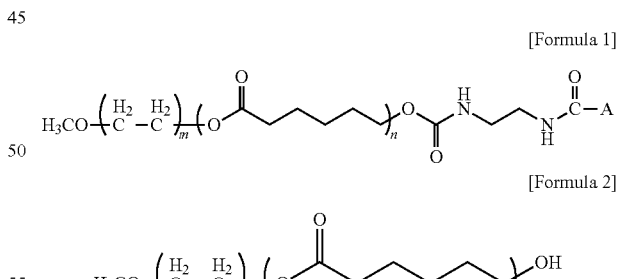

In Formulas 1 and 2, m is in a range of 10 to 20, n is in a range of 15 to 30, and A represents a cell-adhesive peptide.

According to another aspect of the present invention, there is provided a method of preparing a thermosensitive biodegradable hydrogel, which includes mixing a methoxy polyethylene glycol-polycaprolactone (MPEG-PCL) copolymer, to which a cell-adhesive peptide binds, represented by the following Formula 1, and a methoxy polyethylene glycol-polycaprolactone (MPEG-PCL) copolymer represented by the following Formula 2:

According to still another aspect of the present invention, there is provided a tissue engineering support including the above-described thermosensitive biodegradable hydrogel.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 5 is a fluorescence microscope image immediately after treatment, FIGS. 6 to 8 are fluorescence microscope images after 3, 7 and 14 days of the treatment, respectively, and FIGS. 9 and 10 are scanning electron microscope (SEM) images after 7 and 14 days of the treatment, respectively.

In each drawing, (A) is an image of a surface of hydrogel, and (B) is an image of the inside of hydrogel into the mesenchymal stem cells are encapsulated; FIG. 11 is a fluorescence microscope image immediately after treatment, FIGS. 12 to 14 are fluorescence microscope images after 3, 7 and 14 days of the treatment, respectively, and FIGS. 15 and 16 are SEM images after 7 and 14 days of the treatment, respectively.

(A) is an image of a surface of hydrogel in FIGS. 11 to 15, and (B) is an image of the inside of hydrogel into which the mesenchymal stem cells are encapsulated in FIGS. 11 to 16.

Figure 17:
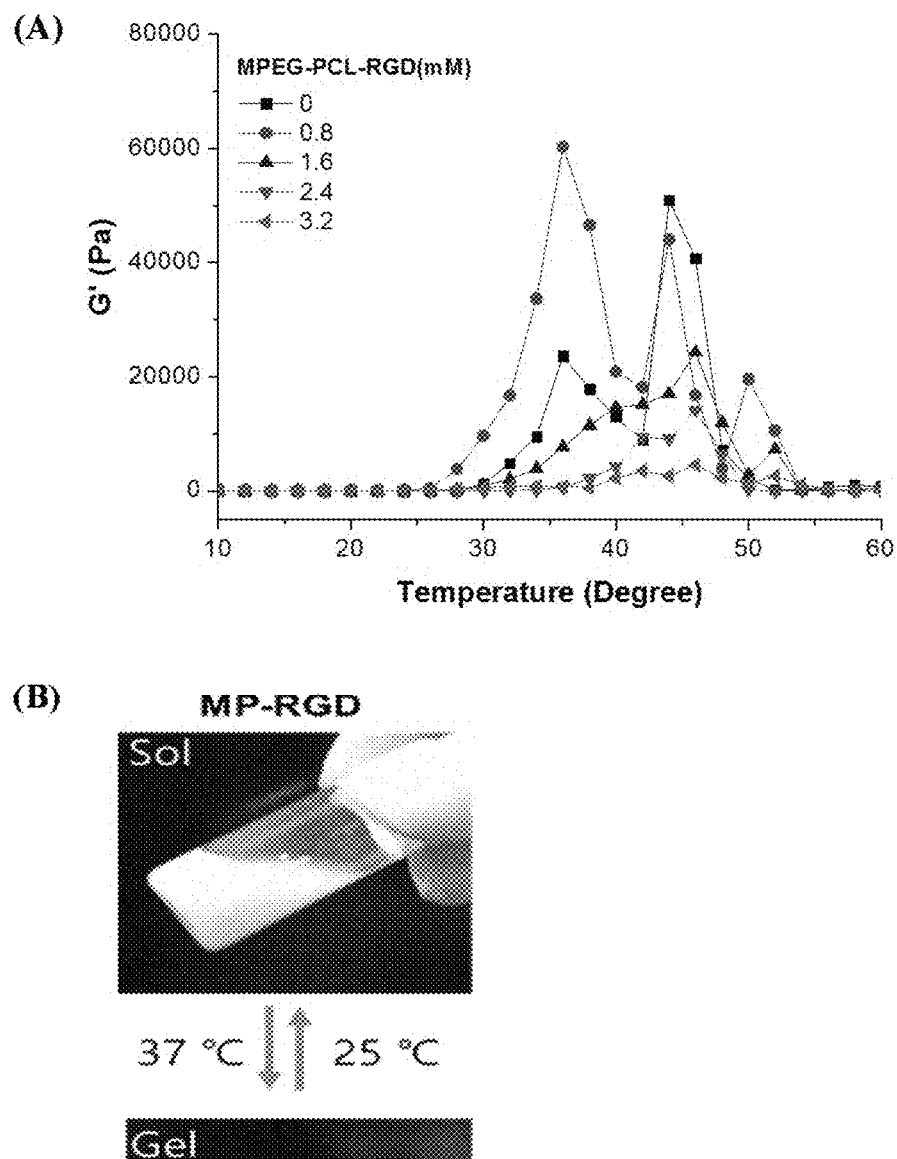

FIG. 17 is (A) a graph illustrating sol-gel phase transition behaviors of MPEG-PCL-RGD and MPEG-PCL hydrogels prepared in Preparative Example 3 of the present invention with the temperature, and (B) an image showing a sol-gel phase transition behavior of the MPEG-PCL-RGD hydrogel at 37° C.

Figure 18:
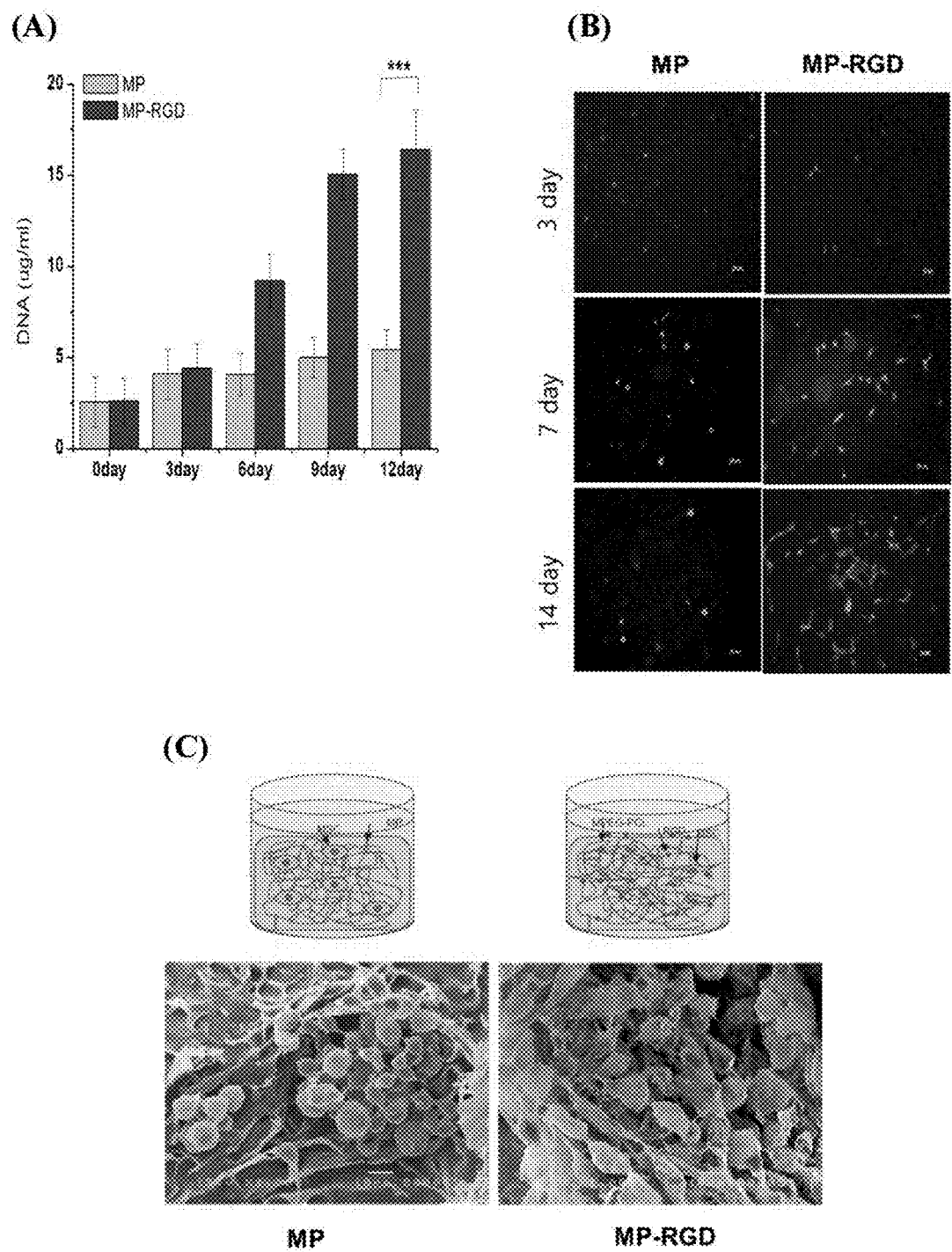

FIG. 18 shows survival and adhesion of MSCs encapsulated in hydrogels prepared in Preparative Example 3 of the present invention. In FIG. 18, MP and MP-RGD indicate MPEG-PCL and MPEG-PCL-RGD hydrogels, respectively. (A) shows a graph illustrating the change of DNA quantification in MSCs encapsulated in MPEG-PCL-RGD hydrogel for 12 days (***p<0.001). (B) shows the fluorescence images (scale bar, 50 µm). (C) shows MSCs morphology using Scanning Electron Microscope.

Figure 19:
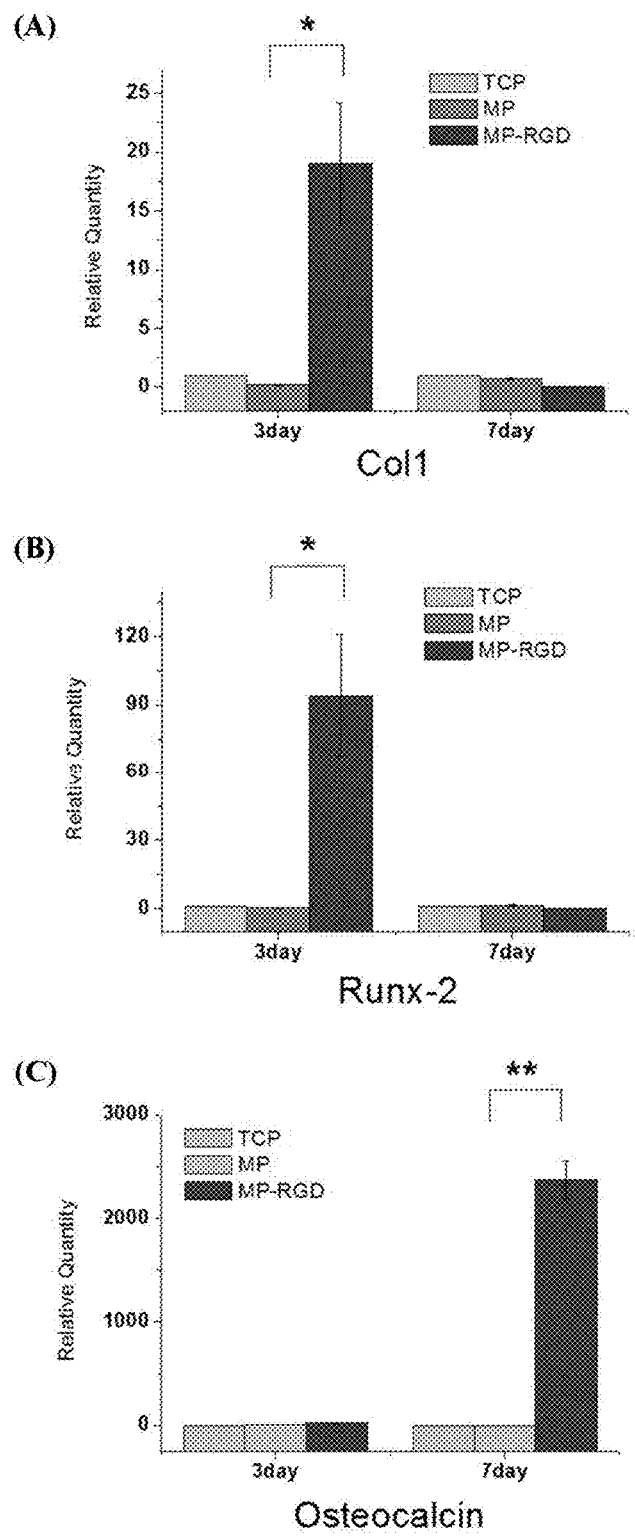
Figure 20:
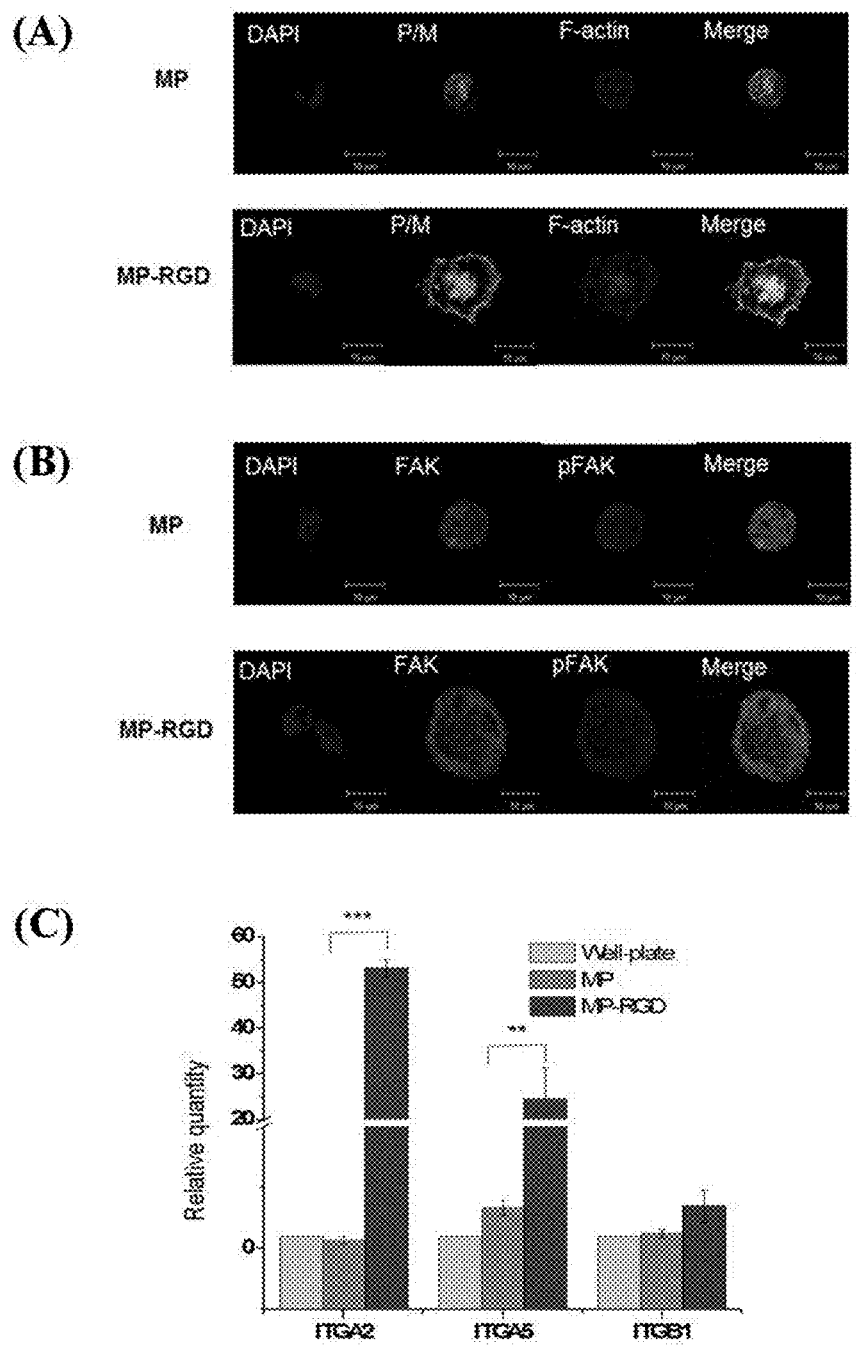

FIGS. 19 and 20 show evaluation of MSCs behavior and osteogenic differentiation in MPEG-PCL-RGD hydrogel prepared in Preparative Example 3 of the present invention. In FIGS. 19 and 20, MP and MP-RGD indicate MPEG-PCL and MPEG-PCL-RGD hydrogels, respectively. FIG. 19 shows the graphs for determination of osteogenic differentiation markers (A) collagen type 1, (B) Runx-2, and (C) osteocalcin (*p<0.001, p<0.01). FIG. 20 shows the fluorescence images for analysis of the expression of (A) F-actin and Plasma membrane (P/M) (scale bar, 10 µm), and (B) focal adhesion kinase (FAK) (scale bar, 10 µm). (C) of FIG. 20 shows a graph for real-time RT-PCR analysis of integrin α2, α5 and β1 expression profiles.

Figure 21:
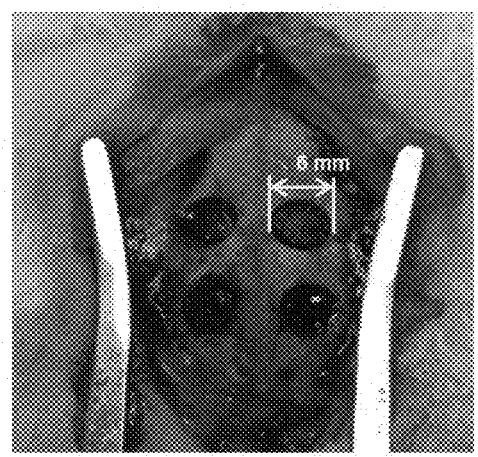
Figure 21:
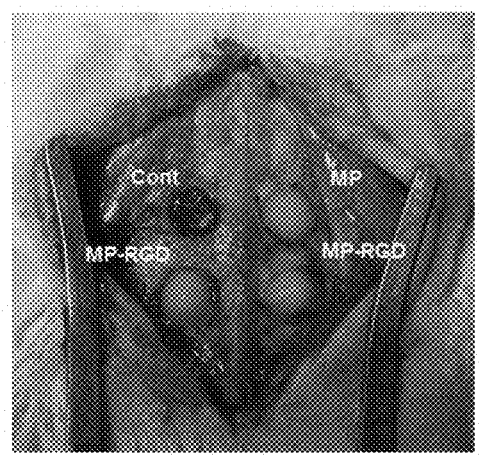

FIG. 21 is the pictures showing implantation of MSCs encapsulated in MPEG-PCL-RGD and MPEG-PCL hydrogels prepared in Preparative Example 3 of the present invention into the rabbit calvarial defects. In FIG. 21, MP and MP-RGD indicate MPEG-PCL and MPEG-PCL-RGD hydrogels, respectively. (A) of FIG. 21 shows defects created using a trephine bur (6 mm—diameter). (B) of FIG. 21 shows grafts containing MSCs encapsulated in each of the hydrogels.

Figure 22:
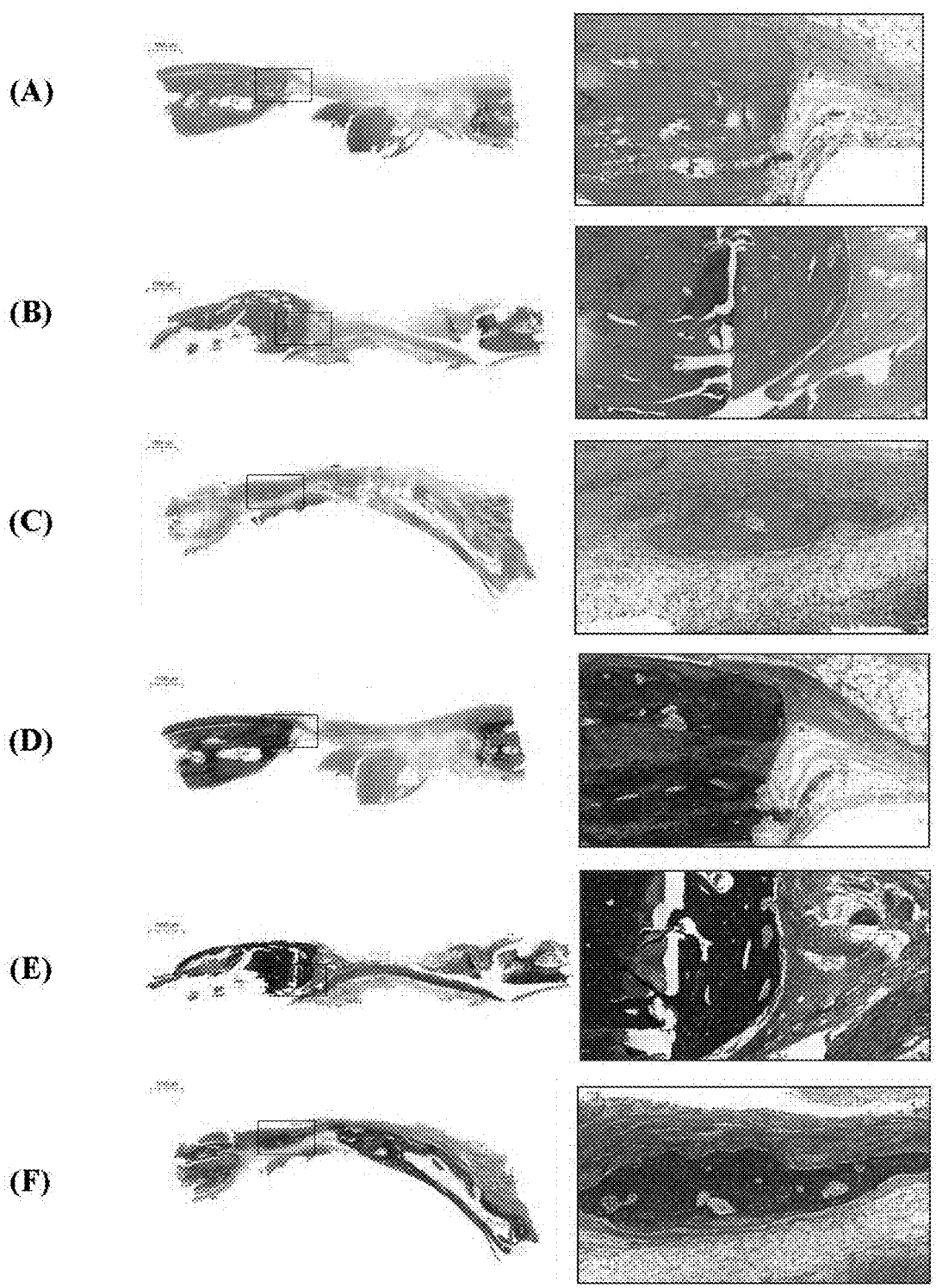

FIG. 22 is the histological images of the rabbit calvarial defects at 6 weeks post-implantation using H&E and Masson's trichrome stains. H&E stain: (A) control, (B) MPEG-PCL, and (C) MPEG-PCL-RGD. Masson's trichrome stain: (D) control, (E) MPEG-PCL, and (F) MPEG-PCL-RGD (scale bar—1000 µm, 100 µm, respectively).

Figure 23:
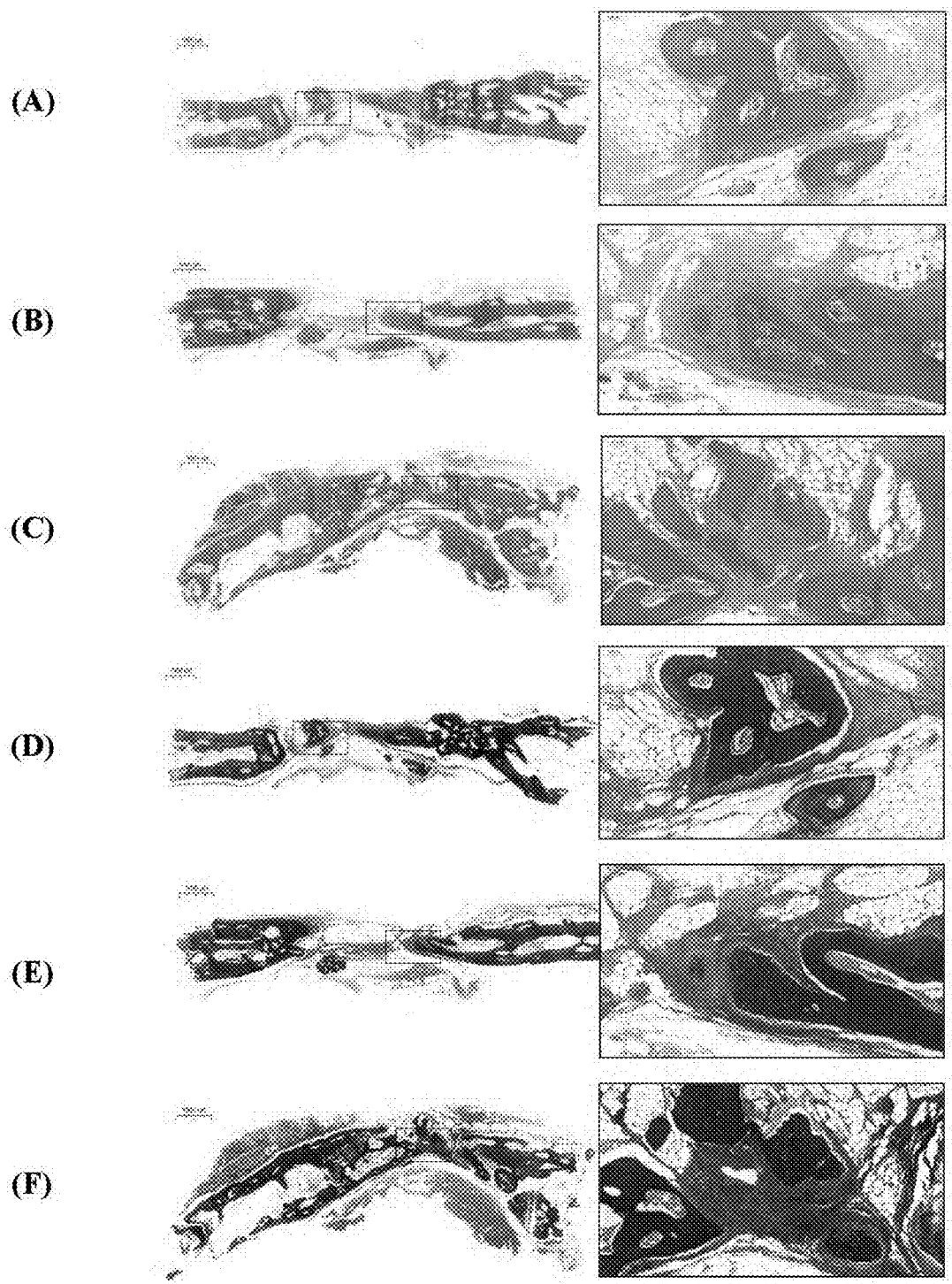

FIG. 23 is the histological images of the rabbit calvarial defects at 12 weeks post-implantation using H&E and Masson's trichrome stains. H&E stain: (A) control, (B) MPEG-PCL, and (C) MPEG-PCL-RGD. Masson's trichrome stain: (D) control, (E) MPEG-PCL, and (F) MPEG-PCL-RGD (scale bar—1000 µm, 100 µm, respectively).

Figure 24:
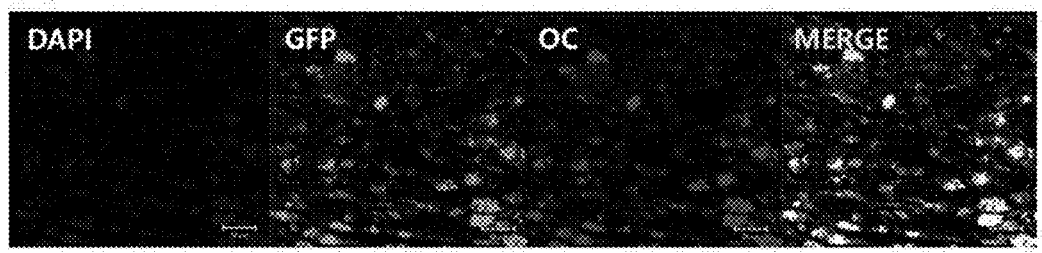
Figure 24:
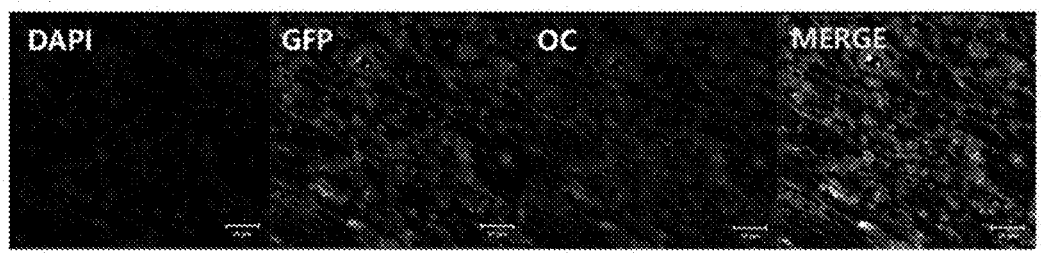
Figure 24:
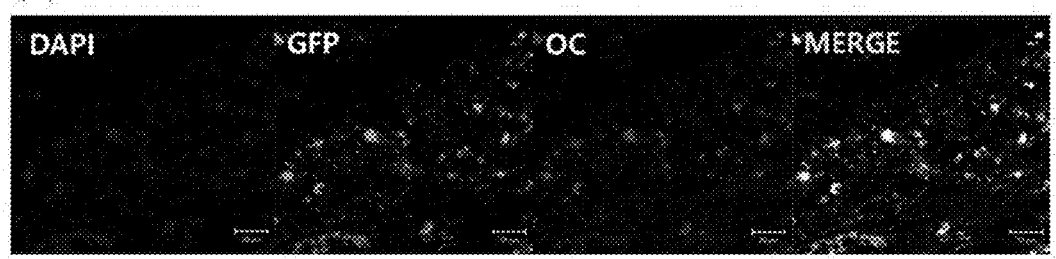
Figure 24:
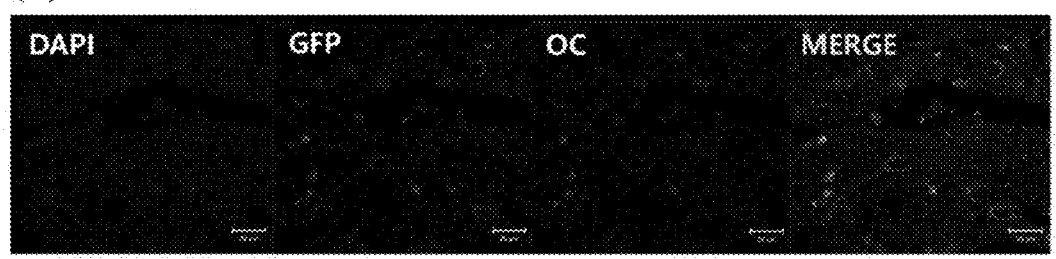

FIG. 24 is the images of immunohistochemical staining for osteocalcin and green fluorescent protein (GFP) within newly formed bone areas in the calvarial defects. After 6 weeks, (A) MPEG-PCL, and (B) MPEG-PCL-RGD. After 12 weeks, (C) MPEG-PCL, and (D) MPEG-PCL-RGD (scale bar—20 µm).

Figure 25:
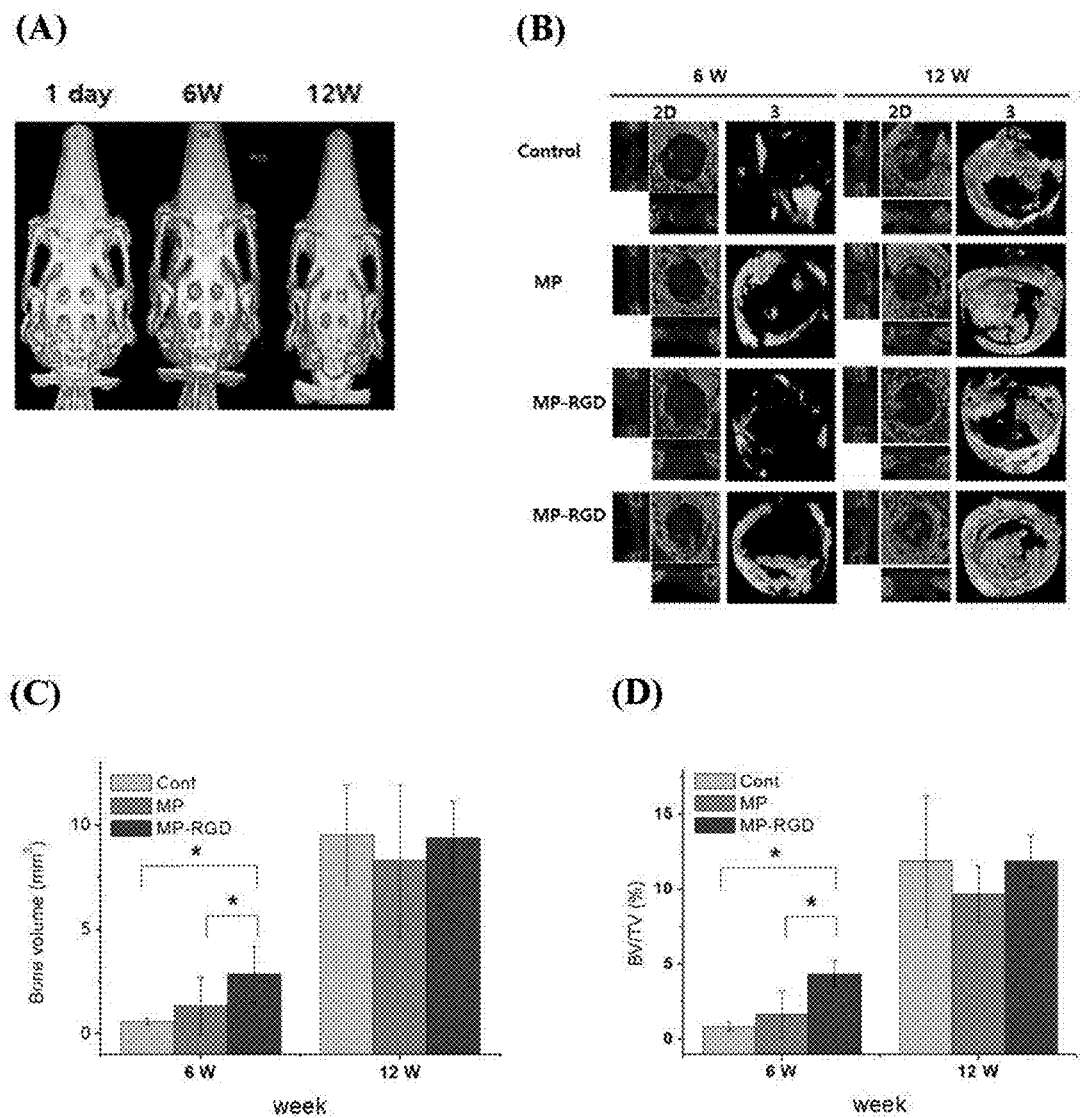

FIG. 25 is the representative CT and µCT images showing bone formation in the calvarial defects. (A) is 3D CT scan images of the calvarium after 1 day, 6 and 12 weeks post implantation. (B) is 2D and 3D µCT images after 6 and 12 weeks post-implantation. (C) and (D) are graphs showing quantitative analysis of Bone volume and bone volume per total volume, respectively (*p<0.05).

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various changes and modifications can be made to the exemplary embodiments of the prevention invention without departing from the scope of the invention.

Unless specifically stated otherwise, all the technical and scientific terms used in this specification have the same meanings as what are generally understood by a person skilled in the related art to which the present invention pertains. In general, the nomenclatures used in this specification and the experimental methods and materials described below are widely known and generally used in the related art.

The present invention provides a thermosensitive biodegradable hydrogel and a use of the thermosensitive biodegradable hydrogel. Here, the thermosensitive biodegradable hydrogel includes a methoxy polyethylene glycol-polycaprolactone (MPEG-PCL) copolymer (hereinafter referred to as a copolymer of Formula 1), to which a cell-adhesive peptide binds, represented by the following Formula 1, and a methoxy polyethylene glycol-polycaprolactone (MPEG-PCL) copolymer (hereinafter referred to as a copolymer of Formula 2) represented by the following Formula 2.

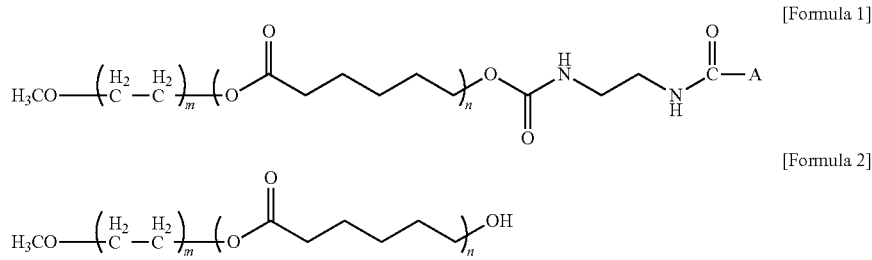

[Formula 1]

[Formula 2]

In Formula 1 and 2, m may be in a range of 10 to 20, 12 to 18, or 15 to 17, n may be in a range of 15 to 30, 20 to 25, or 21 to 24, and A represents a cell-adhesive peptide.

The thermosensitive biodegradable hydrogel according to the present invention has a sol phase showing flow characteristics at room temperature, but has a gel phase at 30 to 50° C., more particularly 35 to 45° C. The thermosensitive biodegradable hydrogel may be easily transplanted into living bodies since the thermosensitive biodegradable hydrogel is present in a sol phase at room temperature due to such characteristics, and may be easily used as a tissue engineering support since the thermosensitive biodegradable hydrogel has a gel phase in vivo.

In the present invention, as the copolymer of Formula 2, the methoxy polyethylene glycol-polycaprolactone (MPEG-PCL) copolymer is a copolymer of a thermosensitive polymer, methoxy polyethylene glycol (MPEG), and a biodegradable polymer, polycaprolactone (PCL).

Since polyethylene glycol (PEG) has many advantages in the drug delivery and tissue engineering fields, the polyethylene glycol (PEG) may serve as a drug delivery system to easily encapsulate and release a drug. Also, polyethylene glycol (PEG) has high solubility in water and an organic solvent, and shows excellent biocompatibility since the polyethylene glycol (PEG) is not toxic and shows no rejection reaction mediated by immune responses. As a substance whose has been approved for use in the human body by the U.S. Food and Drug Administration, polyethylene glycol (PEG) has also been used in the pharmaceutical preparation industry. Among hydrophilic polymers, the PEG has been widely applied as a biomaterial since the PEG has an excellent effect of inhibiting absorption of proteins and serves to improve biocompatibility of blood contact materials. Specifically, methoxy polyethylene glycol (MPEG) may be used as the polyethylene glycol (PEG).

The methoxy polyethylene glycol-polycaprolactone (MPEG-PCL) copolymer is a thermosensitive copolymer that already shows the sol-gel phase transition characteristics, and thus has been applied as a biomaterial in the tissue engineering and drug delivery fields.

In the present invention, the copolymer of Formula 2 may be synthesized in laboratories, etc., and used, or commercially available copolymers may be used as the copolymer of Formula 2.

In the present invention, the copolymer of Formula 1 is a copolymer in which a cell-adhesive peptide binds to the above-described copolymer of Formula 2, particularly a methoxy polyethylene glycol-polycaprolactone (MPEG-PCL) copolymer to which a cell-adhesive peptide binds.

In the present invention, the methoxy polyethylene glycol-polycaprolactone (MPEG-PCL) copolymer to which the cell-adhesive peptide binds may be used to improve cellular adhesiveness in vivo. In the prior art, since polycaprolactone in the methoxy polyethylene glycol-polycaprolactone (MPEG-PCL) copolymer shows a hydrophobic property, the MPEG-PCL copolymer has a difficulty in being absorbed into cells in the body or surfaces of protein polymers. Therefore, in the present invention, when the cell-adhesive peptide is allowed to bind to the MPEG-PCL copolymer, the copolymer may show a hydrophilic property and have an improved activity to bind to the cells.

Such a cell-adhesive peptide that may be used herein may include one or more selected from the group consisting of Arg-Gly-Asp (RGD), Arg-Glu-Asp-Val (REDV), Leu-Asp-Val (LDV), Tyr-Ile-Gly-Ser-Arg (YIGSR), Pro-Asp-Ser-Gly-Arg (PDSGR), Ile-Lys-Val-Ala-Val (IKVAV), and Arg-Asn-Ile-Ala-Glu-Ile-Ile-Lys-Asp-Ala (RNIAEIIKDA).

In the present invention, the copolymer of Formula 1 may be present at a content of 5% by weight or less, 4% by weight or less, or 3% by weight or less, based on 100% by weight of the copolymer of Formula 2. Within this content, the thermosensitive biodegradable hydrogel shows sol-gel phase transition characteristics according to the temperature. Here, when the content of the copolymer is greater than 5% by weight, the thermosensitive biodegradable hydrogel shows no sol-gel phase transition characteristics according to the temperature. The lower limit of the copolymer may be greater than or equal to 0.001% by weight.

The thermosensitive biodegradable hydrogel according to the present invention may be prepared through the step: mixing the methoxy polyethylene glycol-polycaprolactone (MPEG-PCL) copolymer, to which a cell-adhesive peptide binds, represented by Formula 1, and the methoxy polyethylene glycol-polycaprolactone (MPEG-PCL) copolymer represented by Formula 2.

The copolymer of Formula 2, that is, a methoxy polyethylene glycol-polycaprolactone (MPEG-PCL) copolymer may be synthesized in laboratories and used, or commercially available copolymers may be used as the copolymer of Formula 2.

The copolymer of Formula 1 may be prepared by allowing a cell-adhesive peptide to bind to the copolymer of Formula 2 (a methoxy polyethylene glycol-polycaprolactone (MPEG-PCL) copolymer).

Specifically, the copolymer of Formula 1 may be prepared through the steps:

reacting the copolymer of Formula 2 with an imidazole compound;

reacting a diamine compound with the reaction product in the previous step; and reacting a cell-adhesive peptide with the reaction product in the previous step using a condensing agent.

As such, N,N-carbonyldiimidazole may be used as the imidazole compound, and methylenediamine, ethylenediamine or 1,4-aminobutane may be used as the diamine compound.

Also, the condensing agent may be 4-(4,6-dimethoxy-1,3,5-triazin-2-yl)-4-methyl morpholinium chloride (DMT-MM), or 1-ethyl-3-(3-dimethylaminopropyl) carbodiimide (EDC) together with N-hydroxysuccinimide (NHS) can be used as the condensing agent.

The contents of the compounds used in each step and the reaction time in each step may be easily adjusted, and the methoxy polyethylene glycol-polycaprolactone (MPEG-PCL) copolymer to which the cell-adhesive peptide binds may be prepared through the above-described steps.

In the present invention, the copolymer of Formula 1 may be present at a content of 5% by weight or less, 4% by weight or less, or 3% by weight or less, based on 100% by weight of the copolymer of Formula 2, and the lower limit of the copolymer may be greater than or equal to 0.001% by weight.

Also, the present invention provides a method of treating tissue damage, which includes administering the thermosensitive biodegradable hydrogel to a subject suffering from tissue damage.

The thermosensitive biodegradable hydrogel may include cells. Here, the cells may be mesenchymal stem cells, but the present invention is not limited thereto.

Further, the present invention provides a drug delivery system including the thermosensitive biodegradable hydrogel.

The thermosensitive biodegradable hydrogel according to the present invention may be widely applied to tissue engineering and drug delivery systems, etc. In particular, since the thermosensitive biodegradable hydrogel has a structure in which the cell-adhesive peptide binds to the MPEG-PCL copolymer, the thermosensitive biodegradable hydrogel may be used as various types of substrates for the in vitro or in vivo cell and tissue culture when applied to the tissue engineering. Also, the thermosensitive biodegradable hydrogel may be used as a support capable of providing a place to which the cells attach to and grow on, and may be applied as a tissue engineering support including the cells.

Also, the thermosensitive biodegradable hydrogel according to the present invention has a characteristic of being gelated at a body temperature when applied as a biomaterial to the human body, and may also be applied to the uses for the purpose of gelation at a temperature slightly lower or higher than the body temperature.

EXAMPLES

Preparative Example 1: Preparation of Methoxy Polyethylene Glycol-Polycaprolactone (MPEG-PCL) Copolymer (MPEG-PCL-RGD) to which a Cell-Adhesive Peptide Binds 0.4 g ($1.3 \times 10^{-4}$ mol) of MPEG-PCL having a molecular weight of 3,000 g/mol was dissolved in 30 ml of anhydrous dimethyl sulfoxide (DMSO). Thereafter, 0.025 g ($1.56 \times 10^{-4}$ mol) of N,N-carbonyldiimidazole was added thereto, and reacted at room temperature for an hour.

Then, 0.009 g ($1.56 \times 10^{-4}$ mol) of ethylenediamine was added to the resulting mixture, and reacted at room temperature for 5 days. Subsequently, 20 ml of deionized water was added thereto, followed by addition of 0.054 g ($1.56 \times 10^{-4}$ mol) of RGD and 0.043 g ($1.56 \times 10-4$ mol) of 4-(4,6-dimethoxy-1,3,5-triazin-2-yl)-4-methyl morpholinium chloride (DMT-MM), and then reacted at room temperature for 5 days.

Subsequently, the resulting reaction mixture was purified through dialysis for 3 days using MWCO (2K, Spectrum Laboratories, USA), and then freeze-dried.

Figure 1:
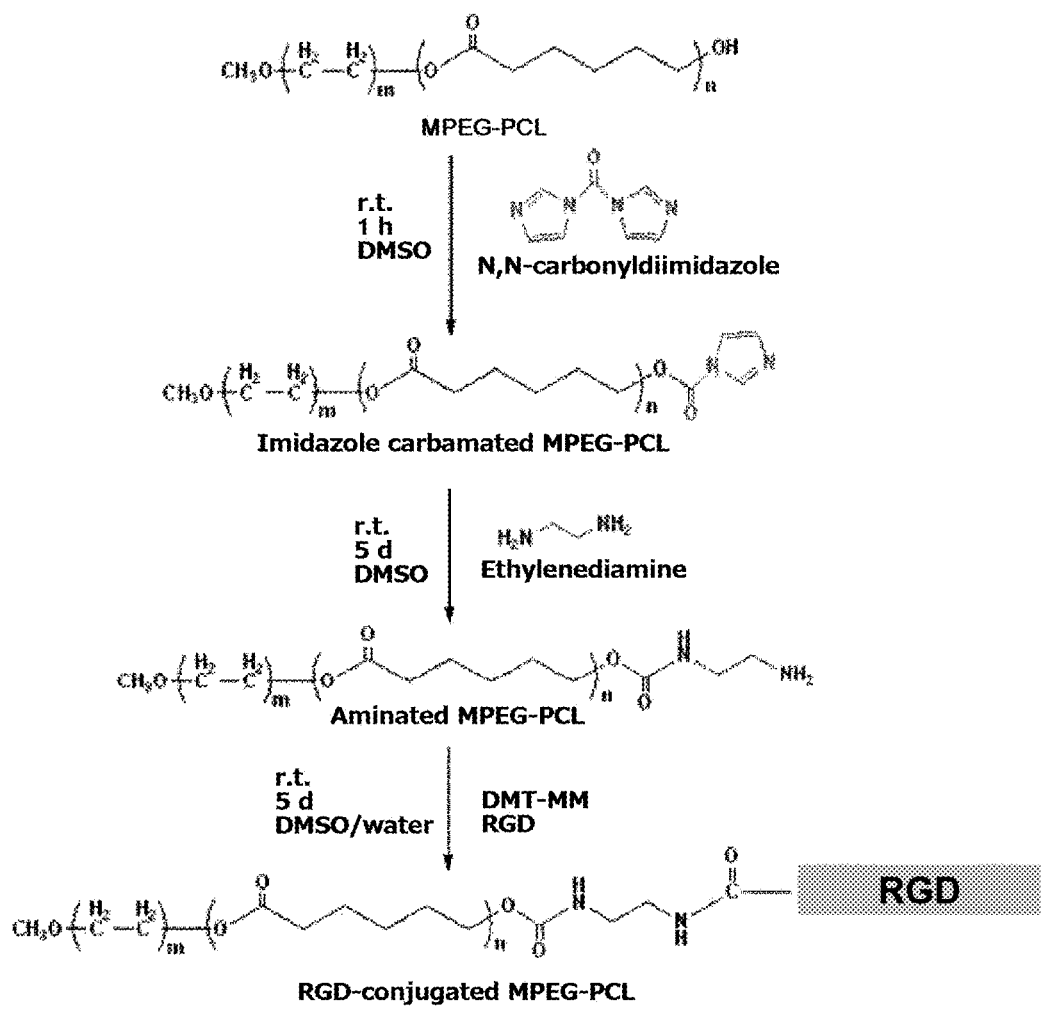
FIG. 1 is a schematic diagram showing a method of preparing MPEG-PCL-RGD (MPEGPCL) to which a cell-adhesive peptide binds according to one exemplary embodiment of the present invention.

The above-described method is shown in FIG. 1. As shown in FIG. 1, N,N-dimethylimidazole, ethylenediamine, and both DMT-MM and a cell-adhesive peptide (RGD) may be sequentially reacted with MPEGPCL to prepare MPEG-PCL to which the cell-adhesive peptide binds (MPEG-PCL-RGD).

Figure 2:
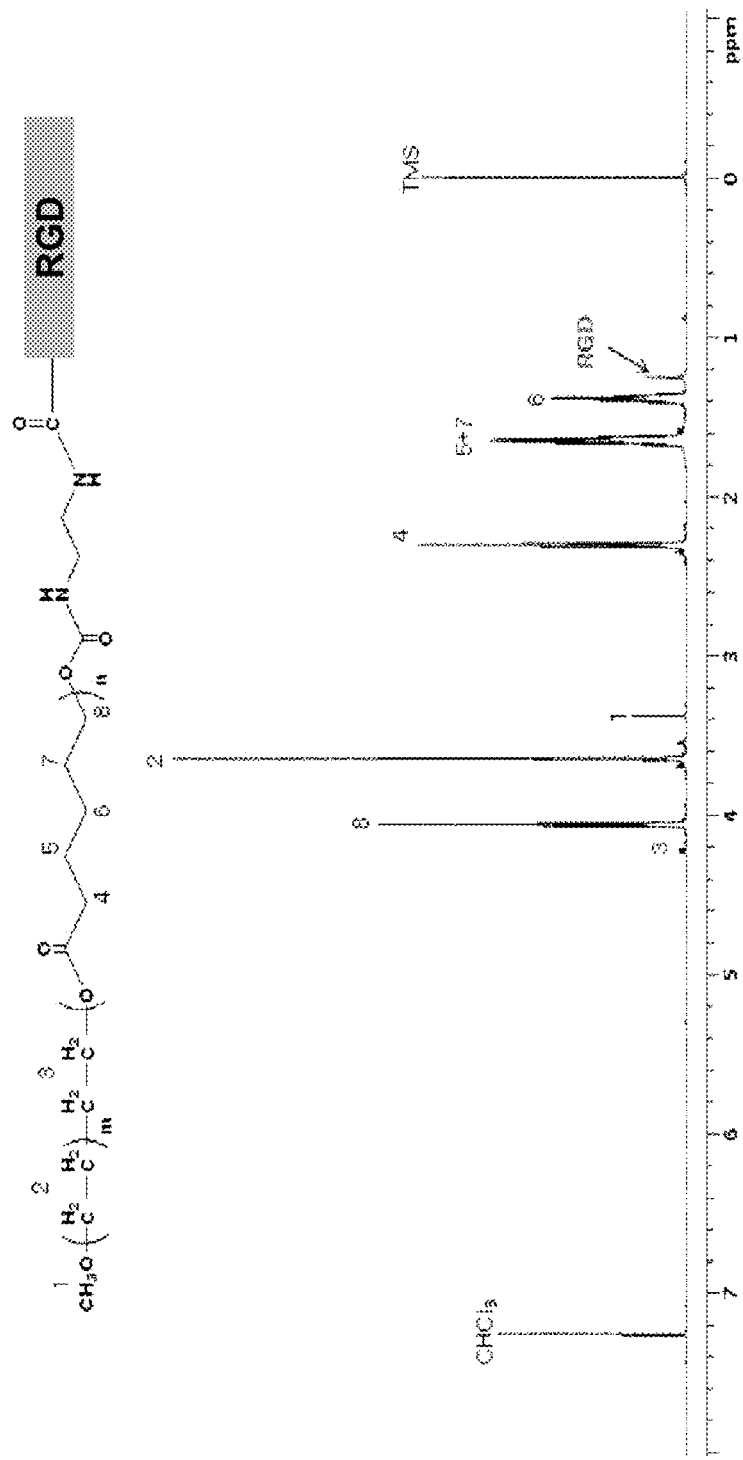
FIG. 2 is a diagram showing the $^1$H NMR spectrum of MPEG-PCL-RGD prepared according to one exemplary embodiment of the present invention.

The $^1$H NMR spectrum of MPEG-PCL-RGD prepared in Preparative Example 1 is shown in FIG. 2. In FIG. 2, certain peaks of the MPEG-PCL-RGD may be observed.

Preparative Example 2: Preparation of Thermosensitive Biodegradable Hydrogel

The MPEG-PCL-RGD prepared in Preparative Example 1 was mixed with MPEG-PCL to prepare a thermosensitive biodegradable hydrogel.

First, 500 mg of MPEG-PCL and 15 mg of MPEG-PCL-RGD (3% by weight, based on 100% by weight of the MPEG-PCL) were added to PBS (pH 7.4, 2.575 ml) to a concentration of 20%, immersed at 80° C. for 5 seconds, and then vortexed 5 times to prepared a slightly bluish suspension, which was then stabilized at 4° C. for 2 days in a refrigerator.

Comparative Example 1

A sol was prepared in the same manner as in Preparative Example 2, except that the MPEG-PCL-RGD was used at a content of 50 mg (10% by weight, based on 100% by weight of the MPEG-PCL).

Experimental Example 1: Confirmation of Sol-Gel Phase Transition Behavior of Thermosensitive Biodegradable Hydrogel The sol-gel phase transition behaviors of the thermosensitive biodegradable hydrogel prepared in Preparative Example 2 and the MPEG-PCL were observed.

Figure 3:
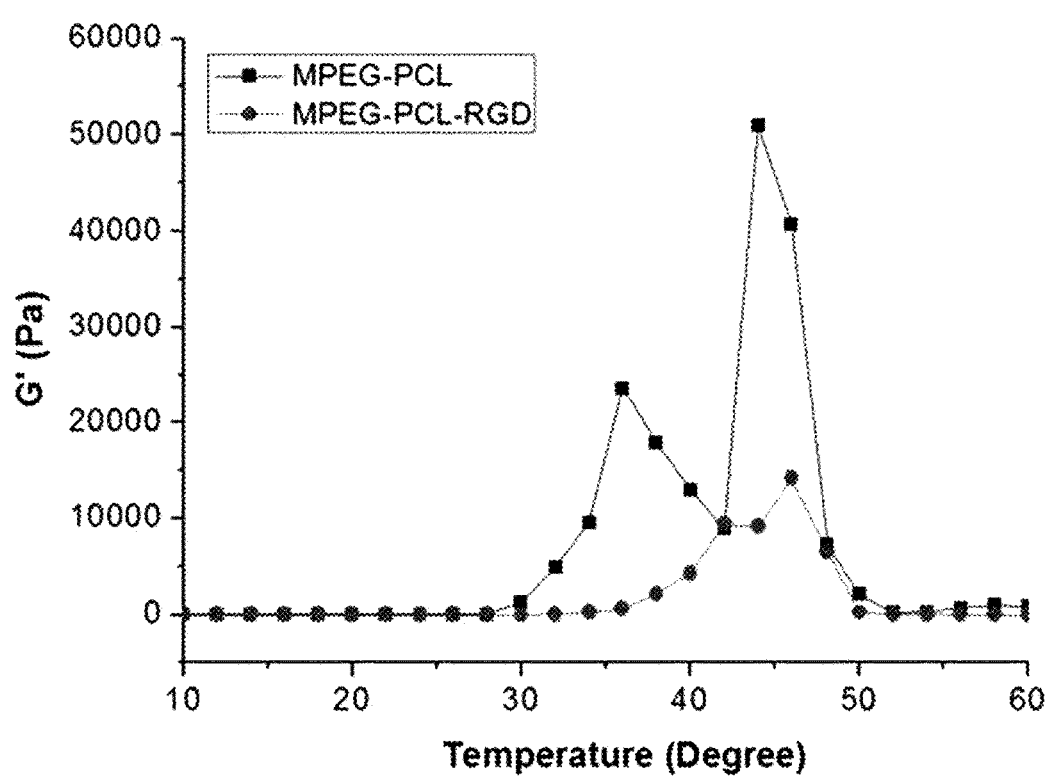
FIG. 3 is a graph illustrating sol-gel phase transition behaviors of a thermosensitive biodegradable hydrogel and MPEG-PCL according to the temperature.

In the present invention, FIG. 3 is a graph illustrating the sol-gel phase transition behaviors of the thermosensitive biodegradable hydrogel according to the temperature and the MPEG-PCL As shown in FIG. 3, it could be seen that the thermosensitive biodegradable hydrogel according to the present invention and the MPEG-PCL had a sol behavior at a temperature less than 30° C. and greater than 50° C., and has a gel behavior at a temperature of 30 to 50° C. In particular, it could be seen that thermosensitive biodegradable hydrogel according to the present invention has a sol-gel phase transition behavior at 35 to 50° C.

Figure 4:
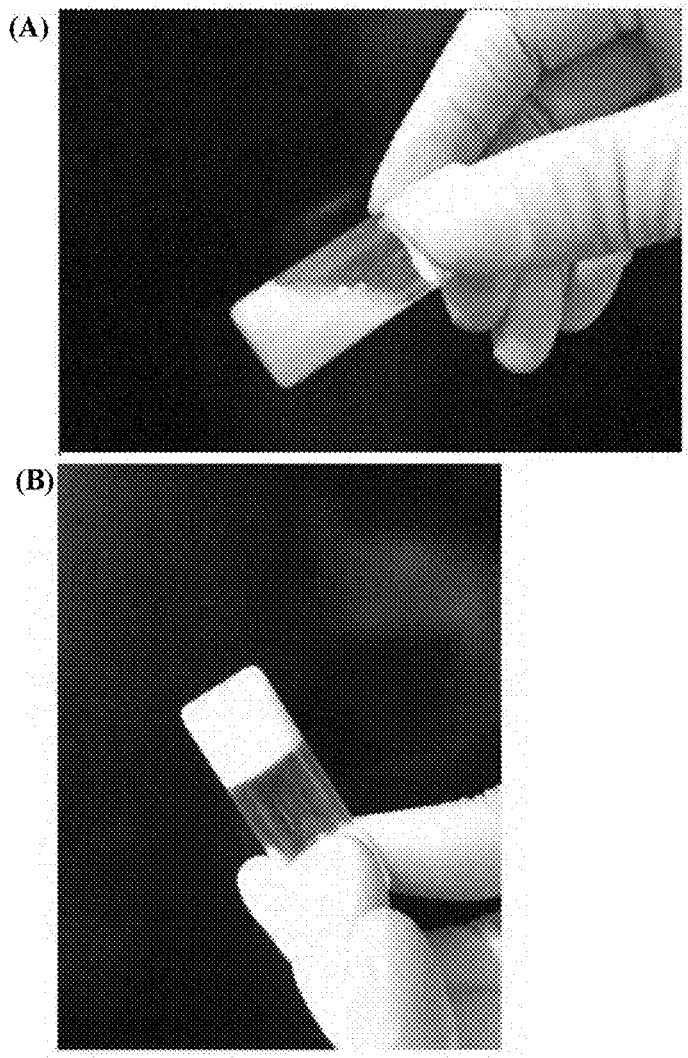
FIG. 4 is an image showing a sol-gel phase transition behavior of the thermosensitive biodegradable hydrogel at 37° C.

Also, FIG. 4 is (A) an image of a sol prepared in Comparative Example 1, and (B) an image of the thermosensitive biodegradable hydrogel having a sol-gel phase transition behavior at 37° C. prepared in Preparative Example 2.

As shown in FIG. 4, it could be seen that the thermosensitive biodegradable hydrogel, in which the MPEG-PCL-RGD was used at a content of 3% by weight, based on 100% by weight of the MPEG-PCL, was present in a gel state at 37° C., but the thermosensitive biodegradable hydrogel, in which the MPEG-PCL-RGD was used at a content of 10% by weight, based on 100% by weight of the MPEG-PCL, was present in a sol state at 37° C.

Experimental Example 2: Confirmation of Cellular Adhesiveness of Thermosensitive Biodegradable Hydrogel To check the engraftment of mesenchymal stem cells (MSCs) on the thermosensitive biodegradable hydrogel prepared in Preparative Example 2 (i.e., a mixture of MPEG-PCL-RGD and MPEG-PCL) and the MPEG-PCL, the mesenchymal stem cells (MSCs) were observed using a fluorescence microscope and SEM.

In the mixture of MPEG-PCL-RGD and MPEG-PCL, the content of MPEG-PCL-RGD was 3% by weight, based on 100% by weight of the MPEGPCL.

The cell engraftment was observed using two methods. In the following, the mixture of MPEG-PCL-RGD and the MPEG-PCL, or the MPEG-PCL was expressed as hydrogel.

(A) Surface of Hydrogel (Surface-Hydrogel)

200 µl of hydrogel was put into a culture dish, and then gelated for an hour. Thereafter, $5 \times 10^6$ cells/ml of mesenchymal stem cells (MSCs) were scattered on the hydrogel in a gel state, and cultured.

(B) Inside of Hydrogel into which Mesenchymal Stem Cells are Encapsulated $5 \times 10^6$ cells/ml of mesenchymal stem cells (MSCs) were mixed with 200 µl of hydrogel, and then gelated for an hour. Thereafter, the resulting mixture was cultured according to the time condition.

The mesenchymal stem cells were cultured on a (A) surface of the hydrogel or cultured in the (B) inside of the hydrogel, and observed for 3, 7, and 14 days. The hydrogel was observed under fluorescence microscope in a state in the cells are alive. Then, a medium was removed, and the hydrogel was washed three timed with PBS, fixed with 2.5% glutaraldehyde, quick-frozen with liquid nitrogen, and freeze-dried. Subsequently, the morphology of the cells grown on the hydrogel was confirmed using SEM.

In the present invention, FIGS. 5 to 10 are diagrams showing the adhesiveness of the hydrogel to the mesenchymal stem cells when MPEG-PCL was used.

Figure 5:
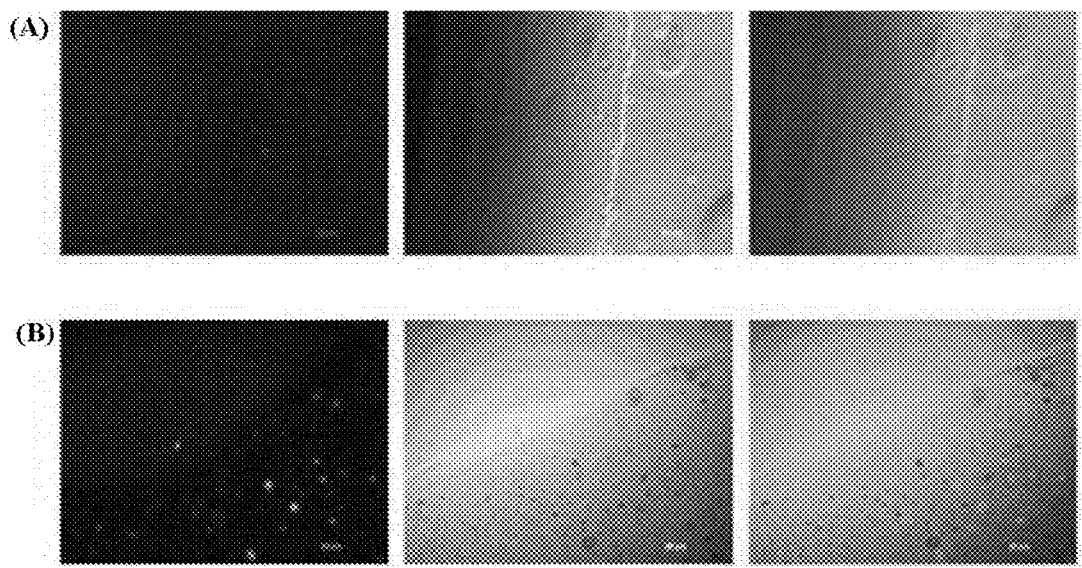
FIGS. 5 to 10 are diagrams showing the adhesiveness of MPEG-PCL to mesenchymal stem cells.
Figure 6:
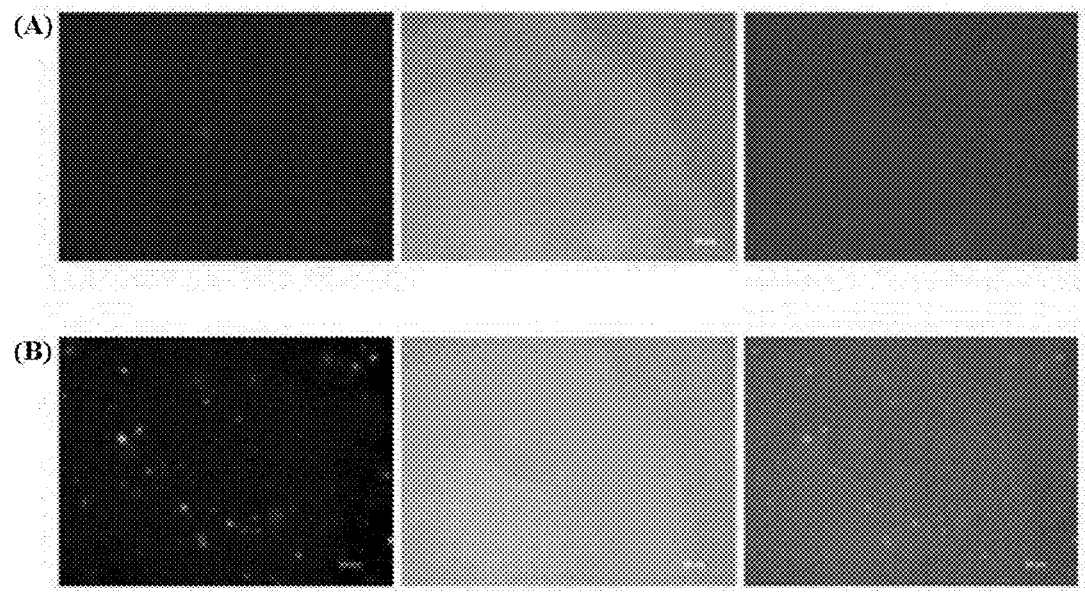
Figure 7:
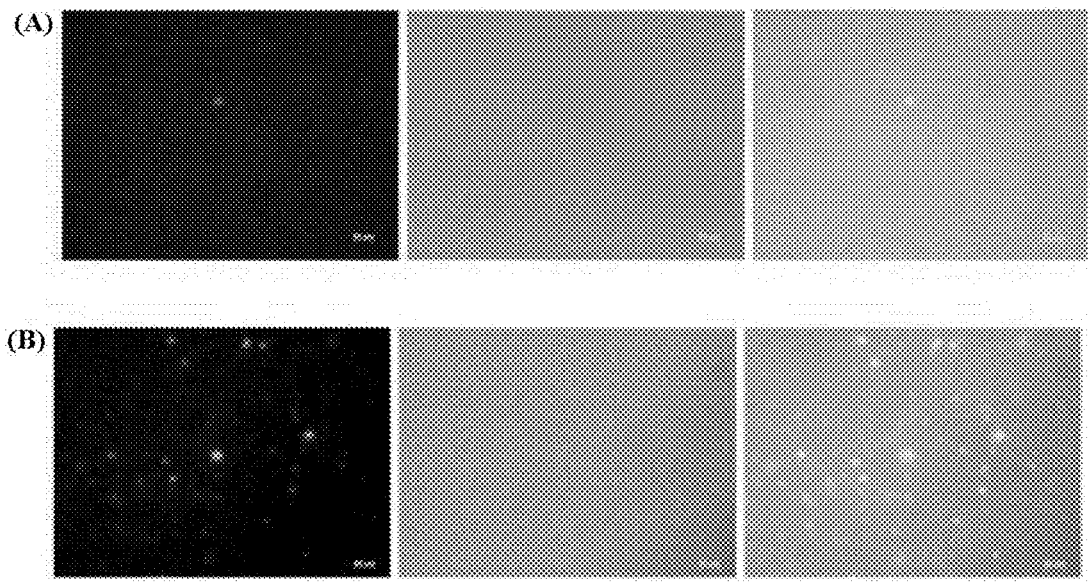
Figure 8:
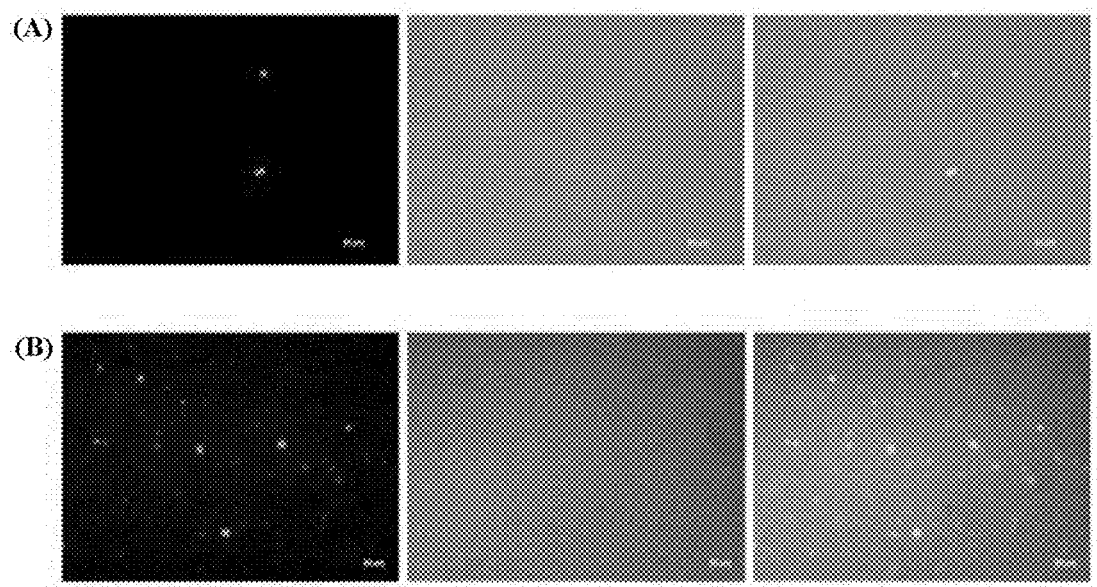

First, in the case of a (A) surface of MPEG-PCL as the hydrogel (surface-hydrogel), it was revealed that the cells were not attached to the surface of the hydrogel immediately after the cells were scattered on the surface of the hydrogel ((A) of FIG. 5), and the cells attached to the surface of the hydrogel were not observed even after 3 days ((A) of FIG. 6), 7 days ((A) of FIG. 7), and 14 days ((A) of FIG. 8), as observed on the fluorescence microscope image.

Figure 9:
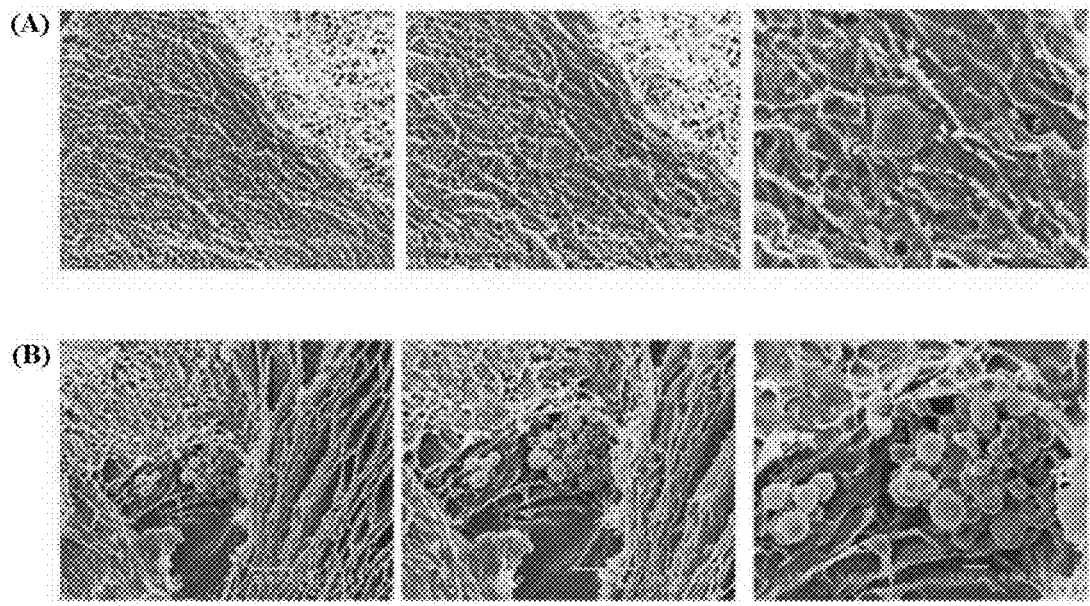
Figure 10:
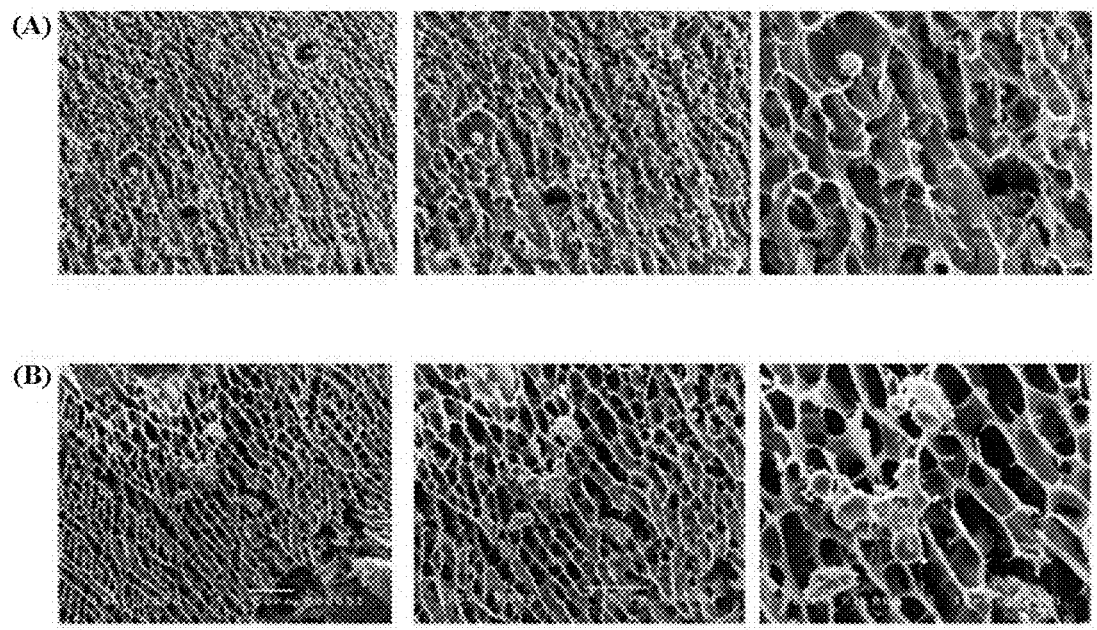

Referring to the SEM image, it was revealed that the cells were attached to each other after 7 days, but a spreading behavior of the cells was not observed ((A) of FIG. 9), and the non-spreading cells were condensed after 14 days, leading to apoptosis of the cells ((A) of FIG. 10).

That is, it could be seen that the cell attachment and division did not easily occur on the (A) surface of the hydrogel (surface-hydrogel) when the MPEG-PCL was used as the hydrogel.

Also, in the case of the (B) inside of MPEG-PCL as the hydrogel into which the mesenchymal stem cells are encapsulated (encapsulation-hydrogel), (B) of FIG. 5 is a fluorescence microscope image immediately after encapsulation of the cells into the hydrogel, and it was revealed that there was no change in the cells after 3 days, as observed on the fluorescence microscope image ((B) of FIG. 6), 7 days ((B) of FIG. 7) and 14 days ((B) of FIG. 8).

Referring to the SEM image, it was revealed that the cells were attached to each other after 7 days, but a behavior of the cells spreading to the hydrogel was not observed ((B) of FIG. 9), and, similar to the (A) surface of the hydrogel, the non-spreading cells were condensed after 14 days, leading to apoptosis of the cells ((B) of FIG. 10).

That is, it could be seen that the cell division did not easily occur on the (B) inside of the hydrogel into which the mesenchymal stem cells are encapsulated (encapsulation-hydrogel) when the MPEG-PCL was used as the hydrogel.

FIGS. 11 to 16 are diagrams showing the adhesiveness of the hydrogel to the mesenchymal stem cells when the mixture of MPEG-PCL-RGD and MPEG-PCL was used as the hydrogel.

Figure 11:
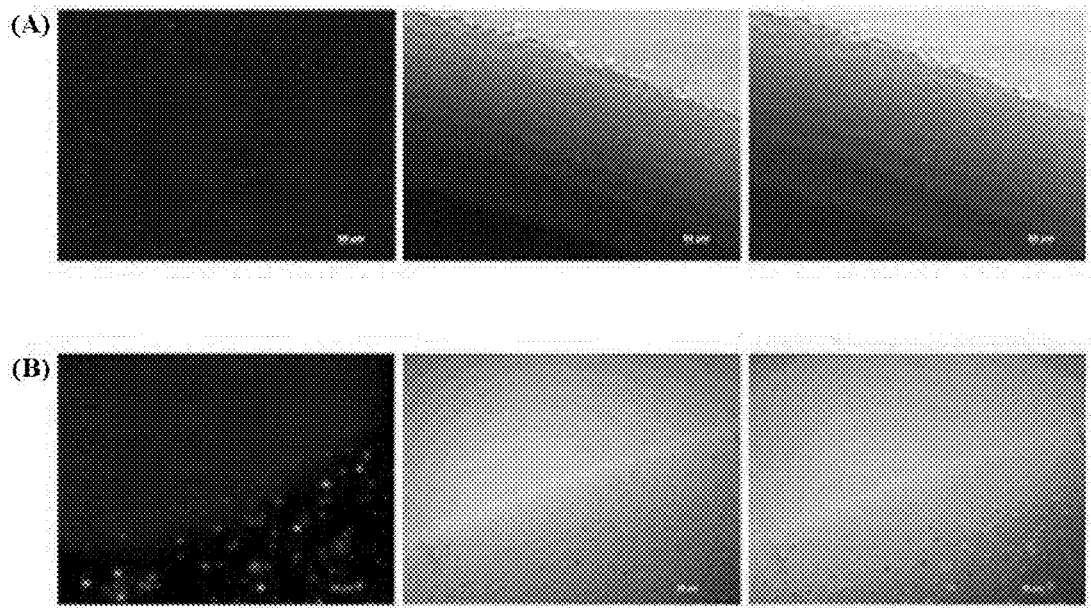
FIGS. 11 to 16 are diagrams showing the adhesiveness of a mixture of MPEG-PCL-RGD and MPEG-PCL to mesenchymal stem cells.
Figure 12:
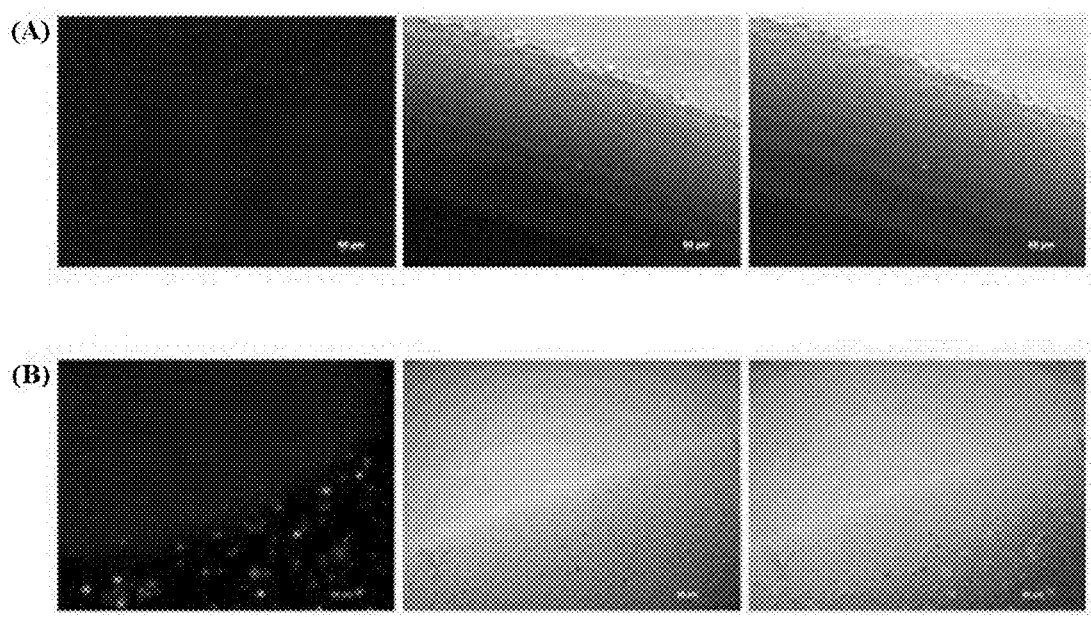
Figure 13:
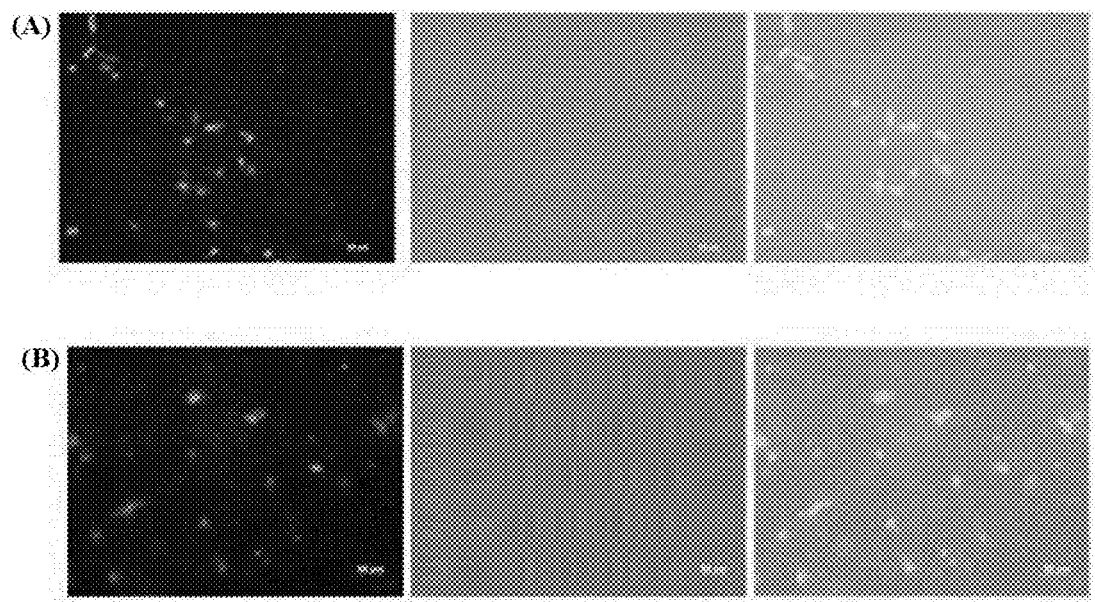
Figure 14:
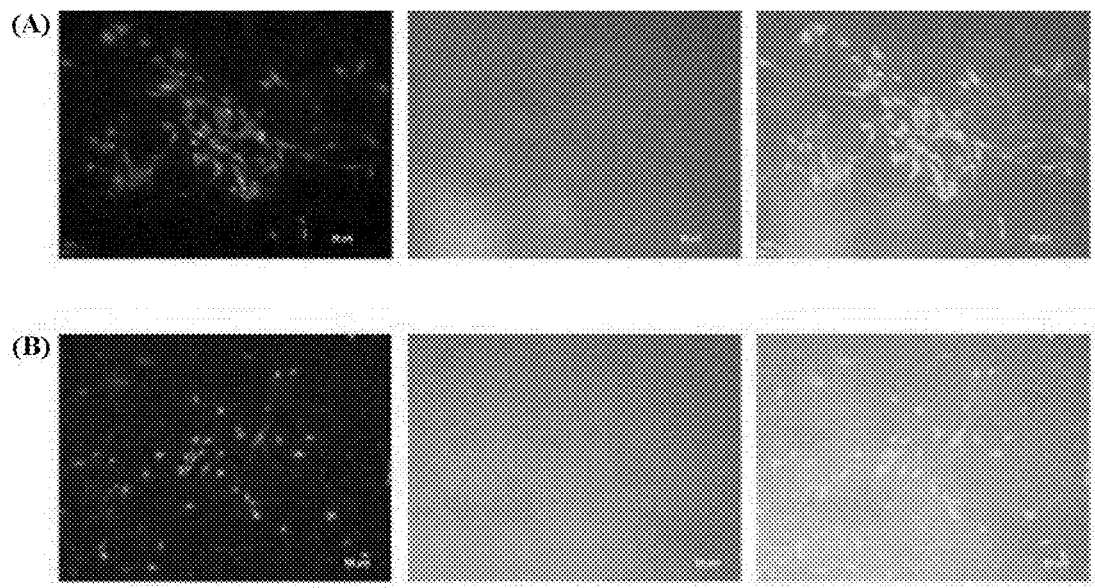

First, in the case of the (A) surface of the hydrogel (surface-hydrogel) as the mixture of MPEG-PCL-RGD and MPEG-PCL, it was revealed that the cells were not still attached to the surface of the hydrogel immediately after the cells were scattered on the surface of the hydrogel ((A) of FIG. 11), as observed on the fluorescence microscope image, but the cells started to be attached to the surface of the hydrogel after 3 days ((A) of FIG. 12), as observed on the fluorescence microscope image. Also, it was revealed that a number of the cells were crowded and further spread after 7 days ((A) of FIG. 13), and the cells spread to communicate with surrounding cells after 14 days ((A) of FIG. 14).

Figure 15:
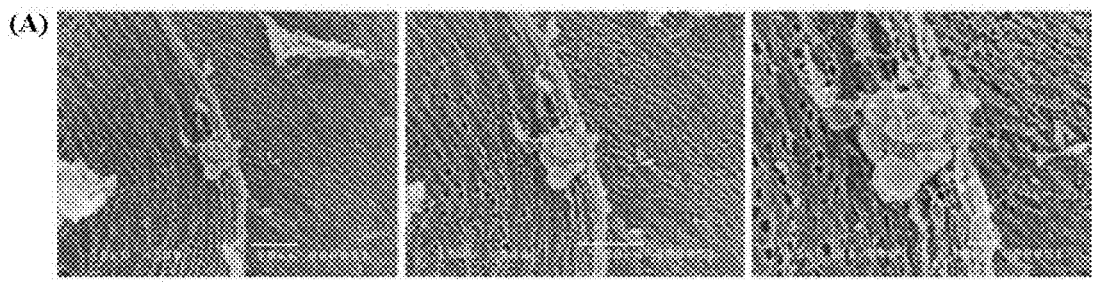

Referring to the SEM image, it could be seen that the cells on the surface of the hydrogel were rigidly attached to the hydrogel after 7 days, and some of the cells were migrated into the hydrogel ((A) of FIG. 15).

That is, it could be seen that the cell attachment and division did not easily occur on the (A) surface of the hydrogel (surface-hydrogel) when the mixture of MPEG-PCL-RGD and MPEG-PCL was used as the hydrogel.

Also, in the case of the (B) inside of the mixture of MPEG-PCL-RGD and MPEG-PCL as the hydrogel into which the mesenchymal stem cells are encapsulated (encapsulation-hydrogel), (B) of FIG. 11 is a fluorescence microscope image immediately after encapsulation of the cells into the hydrogel, and it was revealed that the cells in the hydrogel slowly spread after 3 days, as observed on the fluorescence microscope ((B) of FIG. 12). Also, it was revealed that a number of the cells were attached after 7 days ((B) of FIG. 13), and a number of the cells in the hydrogel started to spread after 14 days ((B) of FIG. 14).

Figure 16:
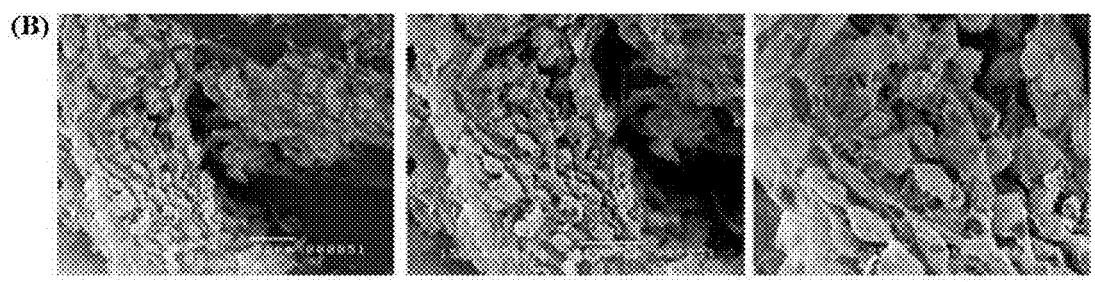

Referring to the SEM image, it could be seen that a number of the cells were crowded and grown to communicate with surrounding cells after 7 days ((B) of FIG. 15), and a number of the cells were grown to come in close contact with each other after 14 days ((B) of FIG. 16).

That is, it could be seen that the cell attachment and division easily occurred on the (B) inside of the hydrogel into which the mesenchymal stem cells are encapsulated (encapsulation-hydrogel) when the mixture of MPEG-PCL-RGD and MPEG-PCL was used as the hydrogel.

Preparative Example 3: Preparation of Thermo-Sensitive Hydrogel

MPEG-PCL-RGD (a final concentration of RGD: 0.8, 1.6, 2.4, and 3.2 mM/ml) was added to MPEG-PCL (500 mg). Thereafter, 2 ml of PBS was put into a vial. To dissolve the resulting mixture, the vial was placed in a water bath set at 80° C. The vial was vigorously stirred until a homogenous solution was formed, and stored at 4° C. for 2 days to be stabilized. A phase transition behavior of the mixture was investigated. Vials containing MPEG-PCL and MPEG-PCL- RGD at different weight ratios were immersed in water bath at 37° C. for an hour, and then cooled to room temperature. The sol-to-gel phase transition of the mixtures was measured using a rheometer (AR 2000 EX; TA Instrument, New Castle, Del., USA). The measurement was carried out as a function of temperature ranging from 10 to 60° C.

As a result, the sol-to-gel phase transition of aqueous hydrogel occurred with a significant change in storage modulus (G'). These results showed that the temperature of gelation gradually increased from 32° C. to 46° C. Especially, at 37° C., the gelation was observed on MPEG-PCL (17.9 kPa) and MPEG-PCL-RGD$_{0.8}$ (46.6 kPa), MPEG-PCL-RGD$_{1.6}$ (11.5 kPa), and MPEG-PCL-RGD$_{2.4}$ (2.2 kPa). On the other hand, the gelation was not observed in the case of MPEG-PCL-RGD$_{3.2}$ (0.6 kPa) ((A) of FIG. 17). In addition, the aqueous solution of MPEG-PCL-RGD$_{2.4}$ showed a reversible phase transition in a temperature-dependent fashion. The solution of MPEG-PCL-RGD$_{2.4}$ flowed freely at 25° C., but turned into a gel state at 37° C. ((B) of FIG. 17). The results showed that the threshold temperature of MPEG-PCL-RGD$_{2.4}$ for gelation was 37° C. Thus, the MPEG-PCL-RGD$_{2.4}$ was subsequently used in Experimental Examples 3 to 10, and hereinafter simply expressed as "MPEG-PCL-RGD."

Experimental Example 3: Proliferation of MSCs on Hydrogel 3.1. Rabbit MSC Culture Rabbit bone marrow-derived mesenchymal stem cells (MSCs) were purchased from OriCell™ rabbit mesenchymal stem cells (Cyagen Biosciences Inc. CA. USA). MSCs were cultured in OriCell™ MSC growth medium supplemented with 10% FBS, L-glutamine, and a penicillin streptomycin solution using a humidified incubator maintained at 5% $CO_2$. The cells were passaged when the cell reached a confluence of 80 to 90%. For subculture, the cells were detached with 0.25% trypsin-EDTA. Then, the medium was replaced every 3 days. The cells between passages 3 and 7 were used for the studies described in the following experiments.

3.2. Encapsulation of MSCs into Hydrogels for In Vitro Test

MSCs were detached from culture flask with trypsin-EDTA and centrifuged to form a pellet ($1\times10^6$ cells per pellet). MSCs were encapsulated into the MPEG-PCL or MPEG-PCL-RGD hydrogel obtained from Preparative Example 3. The cell pellet was re-suspended in 1 ml of a hydrogel solution with gentle mixing using a vortexer. To form hydrogel in a gel state, the cell-hydrogel mixture was incubated at 37° C. for an hour. A fresh medium was added onto the mixture in a plate. The culture medium was replaced twice a week.

3.3. Proliferation of MSCs in Hydrogel

The proliferation of MSCs in hydrogel was studied using a PicoGreen assay (Invitrogen, CA, USA). In brief, MSCs were mixed with 0.5 ml of the MPEG-PCL or MPEG-PCL-RGD hydrogel obtained from Preparative Example 3 at a density of $1\times10^4$ cells/ml. The cell-laden hydrogel mixture with a volume of 50 μl was cultured in a 96-well plate and added to 200 ml of a growth medium. The medium was replaced every third day for 12 days. On the day of the experiment, the hydrogel was taken out and washed with PBS. Subsequently, each hydrogel was placed in an Eppendorf tube and stored at −80° C. until the DNA extraction was achieved. After thawing, MSCs in the hydrogel were digested by addition of proteinase K (Sigma-Aldrich, MO, USA) for 24 hours at 58° C. A solution of the digested hydrogel was collected into new Eppendorf tubes, and centrifuged at ×6000 g. The supernatant was diluted to a final volume of 100 μl, and 100 μl of a PicoGreen reagent was added thereto. Each sample was incubated for 2 to 5 minutes at room temperature while being protected from light. The specimens were placed onto a new 96-well plate. The fluorescence of the sample was measured using Fluorometer (Synergy MX, Bio-Tek, VT, USA). The samples were excited at 480 nm, and emission intensities of the samples were measured at 520 nm.

As a result, the DNA contents of the MSCs encapsulated in MPEG-PCL and MPEG-PCL-RGD were maintained at similar levels for initial 3 days (4 and 4.3 μg/ml, respectively). The proliferation rate of the MSCs cultured on the MPEG-PCL-RGD was significantly increased from the day 6 (2.2 times higher than that of MPEG-PCL). On the day 12, the DNA content of MSCs cultured on the MPEG-PCL-RGD was three-fold or more higher than that of MSCs cultured on the MPEG-PCL. However, the DNA content of MSCs encapsulated in MPEG-PCL showed that no significant differences occurred at all the test period ((A) of FIG. 18). Increase of the DNA content in MPEG-PCL-RGD group suggested that RGD peptide has remarkable effect on MSCs survival.

Experimental Example 4. Fluorescence Microscopy and Scanning Electron Microscopy for MSCs Spreading and Adhesion in Hydrogels 4.1. GFP Transduction to MSCs Using Lentiviral Particles Pre-made GFP lentiviruses (GFP (CMV-Bsd) lentiviral particles, Gentarget Inc. CA. USA) were purchased. MSCs were seeded at $2\times10^6$ cells/ml in a T75 flask and grown for overnight. For the GFP transduction, the media was removed and replaced with 5 ml of transduction media consisting of OriCell™ MSC Growth Medium with 10% FBS and 200 ml of GFP lentiviral particles. GFP-positive MSCs were observed by using a fluorescence microscope (Olympus, Tokyo, Japan). GFP signals were visualized at 72 hours after transduction. The GFP-MSCs from each passage were cultured until sufficient cells for experiments were obtained. Transduction efficiency of GFP was greater than 90%.

4.2. Fluorescence Microscopy and Scanning Electron Microscopy for MSCs Spreading and Adhesion in Hydrogel For analyzing spreading morphology of MSCs in hydrogel, GFP-MSCs encapsulated in MPEG-PCL or MPEG-PCL-RGD hydrogel were cultured in 24-well tissue culture plates for 0, 3, 7, and 14 days and assessed by fluorescent imaging (Axiovert 200, Zeiss, Germany). For scanning electron microscopic analysis, cells in the hydrogel were washed three times with PBS, fixed in 2.5% glutaraldehyde for 24 hours, frozen in liquid nitrogen, and then freeze-dried. To observe the inside of hydrogels, dried hydrogels were cut into a cross-section. The cross-sectional samples were mounted in the metal stubs, and coated with gold. Images were obtained using Scanning electron microscope (SEM; JSM LV 5410, Jeol, Tokyo, Japan).

As a result, MSCs were beginning to spread in MPEG-PCL-RGD hydrogel at the day 3. After the day 7, spindle-like morphology was observed for the MSCs in MPEG-PCL-RGD hydrogel, but only circular morphology was observed for the MSCs in MPEG-PCL hydrogel as in the case of suspended cells ((B) of FIG. 18). SEM analysis was also performed to find the cell-hydrogel interactions ((C) of FIG. 18). SEM images showed that MSCs in MPEG-PCL-RGD hydrogel exhibited elongated morphology and adopted cell-cell and cell-matrix interactions, whereas MSCs in MPEG-PCL hydrogel only presented round-shaped morphology. These results indicated that RGD was involved in the promotion of MSCs adhesion and spreading.

Experimental Example 5. Osteogenic Differentiation of MSCs in Hydrogel

MSCs were encapsulated in hydrogel at a density of $1 \times 10^3$ cells/ml on a 24 well culture plate. On the next day, MSCs encapsulated in hydrogel were exposed to StemPro osteogenic differentiation media (Gibco, MO, USA), and were cultured for up to 21 days in the osteogenic media. The medium was replaced every 3 days for 3 weeks until the end of the experiments. The osteogenic differentiation was evaluated by reverse transcription PCR. The experiments were repeated three times.

As a result, expression of collagen 1, a crucial osteogenic marker, was increased in MSCs encapsulated in MPEG-PCL-RGD hydrogel ((A) of FIG. 19). Runt-related transcription factor 2 (Runx-2) was critical regulator in osteogenic differentiation, and Osteocalcin had an important role in mineralization ((B) and (C) of FIG. 19). These results showed that gene expressions of collagen 1, Runx-2 and osteocalcin were increased for MSCs in MPEG-PCL-RGD hydrogel compared to tissue culture plate (TCP) and MSCs in MPEG-PCL hydrogel. At the day 3, the expression levels of collagen 1, Runx-2 and osteocalcin increased up to $22.2 \pm 1.6$, $94.0 \pm 26.8$ and $18.9 \pm 5.1$-fold, respectively. At the day 7, osteocalcin was significantly up-regulated for MSCs in MPEG-PCL-RGD hydrogel. Thus, conjugation of RGD to the MPEG-PCL significantly induced gene expression of osteogenic markers involved in MSC differentiation. These results indicated that osteogenic differentiation of MSCs was remarkably enhanced by MPEG-PCL-RGD hydrogel.

Experimental Example 6. Spatial Spreading and FAK/pFAK Expression of MSCs in Hydrogel To examine the cellular structure and focal adhesion formation of MSCs in hydrogel, fluorescence staining with phalloidin/WGA and anti-FAK/pFAK was performed. At predetermined time point, the samples were harvested and embedded using the iP-gel kit (Genostaff Co., ltd, Tokyo, Japan) according to the manufacturer's protocol. The prepared samples were fixed in 10% formalin at 4° C. overnight. Fixed samples were made into paraffin blocks following standard protocols. Each paraffin block was sectioned into 4 µm slices. To visualize morphology and focal adhesion of MSCs inside hydrogels, phalloidin-rhodamine (Thermo Fisher Scientific Inc., MA, USA)/wheat germ agglutinin-FITC (WGA; Thermo Fisher Scientific Inc., MA, USA) staining and immunofluorescence staining of FAK and phosphorylated FAK (pFAK) were performed, respectively. Phalloidin/WGA was stained according to the manufacturer's instruction. The immunostaining procedure was performed as described in the previously report. The sections were incubated at 4° C. overnight with FAK and pFAK primary antibodies (Santa Cruz Biotechnology, CA, USA). The fluorescence-labeled secondary antibodies (Santa Cruz Biotechnology, CA, USA) were used as described in the manufacturer's manual. For counterstaining, 4',6'-diamindino-2-phenylindole (DAPI, Thermo Fisher Scientific, Germany) was used.

When RGD binds to integrins at their extracellular domain, it can stimulate the formation of focal adhesion complex through their cytoplasmic domain. Thus, RGD can influence the organization of the F-actin and a component of focal adhesion. Since focal adhesions are generally localized at the edge of the filopodia, the change of transmembrane shape was observed ((A) of FIG. 20). The signals of F-actin (red) increased in MSCs in MPEG-PCL-RGD hydrogel compared to that of the MPEG-PCL hydrogel. Plasma membrane staining (green) revealed outer layer protrusions of the cells encapsulated in MPEG-PCL-RGD hydrogel. These protrusions were only present in the cells of MPEG-PCL-RGD hydrogel, indicating the presence of RGD-integrin interaction. Furthermore, the presence of MPEG-PCL-RGD resulted in a greater degree of MSCs spreading in comparison with MPEG-PCL hydrogel. The signaling of focal adhesion complex, including integrin and FAK, was influenced by RGD. Integrins are important for the induction of FAK phosphorylation. Remarkably, phosphorylated FAK was detected at MSCs encapsulated in MPEG-PCL-RGD hydrogel ((B) of FIG. 20).

Experimental Example 7. Quantitative Gene Expression Using Real-Time PCR

To investigate the expression of $\alpha 2$, $\alpha 5$ and $\beta 1$ integrin subtypes in MSCs in hydrogel, real-time PCR was performed. Hydrogel samples with MSCs were soaked in 1 ml of TRIzol Reagent (Invitrogen, CA, USA) and homogenized for RNA extraction. Purified RNA samples were then reverse-transcribed to cDNA using the SuperScriptIII first-strand synthesis system for RT-PCR kit (Invitrogen, CA, USA). The final cDNAs were subjected to real-time PCR (CFX96™ Real-Time PCR). The PCR primers are listed in Table 1.

TABLE 1

Nucleotide Sequence for primer used in real-time PCR

| Gene name | GeneBank accession number | Primer sequence (5'→3') | Product size (bp) |
|---|---|---|---|
| GAPDH | NM_001082253.1 | GGAATCCACTGGCGTCTTCA TACTTCTCGTGGTTCACGCC | 132 |
| Integrin α2 (ITGA2) | XM_008262194.1 | TGCTGCTGTACACCTGATGG TGTACCCCACCCCACATACA | 141 |
| Integrin α5 (ITGA5) | XM_002711037.2 | CTCCTTCTTCGGCTTCTCGG GCCCAGGGACAGAAGTAGAC | 135 |
| Integrin β1 (ITGB1) | XM_002721189.3 | TCAAGAGTCTCGGGACGGAT CTCACTCGTGCAAGGGTTCT | 146 |

TABLE 1-continued

Nucleotide Sequence for primer used in real-time PCR

| Gene name | GeneBank accession number | Primer sequence (5'→3') | Product size (bp) |
|---|---|---|---|
| Runx-2 | XM_008262992.1 | CTCAGCCATTCTGAAGCCCA CCCCTCGATTGTTATCGGCA | 128 |
| COL1 | XM_008271783.1 | GCGTCCGATCTGTGAAGACA CTCCTGTGGTTTCCTGGTCC | 117 |
| osteocalcin | XM_002715383.2 | CTTCGTGTCCAAGAGGGAGG CTCCAGGGGATCCGGGTAA | 100 |

As a result, the expression of integrin subunits were elevated under the presence of MPEG-PCL-RGD (α2 with 53.3±1.8, α5 with 24.6±6.7 and β1 with 3.4±1.3-fold increase), whereas little changes in the expression of integrin subunits were observed in the absence of RGD (α2 with 0.6±0.3, α5 with 3.3±0.6 and β1 with 1.2±0.3-fold increase) ((C) of FIG. 20). These results indicate that MSCs interacted with MPEG-PCL-RGD and RGD had induced integrin-mediated signaling.

Experimental Example 8. Generation of Calvarial Defect in Animals

New Zealand white rabbits (Orient Bio Inc., Seongnam, Korea) weighing about 4 kg were used in this experiment. To evaluate the influences of the MPEG-PCL-RGD for bone regeneration, 6 mm defects were created on the calvarium of the rabbits ((A) of FIG. 21). The animals were divided into the following 3 groups: (1) MSCs laden MPEg-PCL group, (2) MSCs laden MPEG-PCL-RGD group, and (3) negative-control (empty) group ((B) of FIG. 21). To create calvarial defect, rabbits were anesthetized by intramuscular injection of Zoletil® (Virbac, Carros, France) and Rompun® (Bayer, Leverkusen, Germany). Prior to making the incision, 2 ml of 2% (w/v) lidocaine (Huons, Seoul, Korea) was injected for local pain relief. After incision in the scalp, calvarial defects of 6 mm diameter were created by trephine bur. Each hydrogel was gently inserted into the defect. The incision of scalp was closed with a vicryl suture. At 6 and 12 weeks after hydrogel insertion, rabbits were sacrificed and calvarias were harvested. Harvested calvarial tissues were placed into 10% formalin for overnight and prepared for CT and histological analysis.

Experimental Example 9. Histological and Immunohistochemical Analysis

Formalin-fixed samples were decalcified in Calci-clear rapid (National Diagnostics, GA, USA) for a week, dehydrated through gradient alcohols and embedded in paraffin. The paraffin blocks thus formed were sliced into 4 μm thickness. The slices were stained with Hematoxylin & Eosin and Masson's trichrome. In addition, immunohistochemistry of the samples was performed using primary antibodies for GFP, osteocalcin and collagen 1 (Abcam, Cambridge, UK), respectively. The nuclei were counterstained using DAPI. Bright field images were acquired using slide scanner (Pannoramic MIDI, 3D HISTECH, Budapest, Hungary), and immunofluorescence images were obtained by confocal microscope (LSM800 with Airyscan, Zeiss, Germany).

As a result, Hematoxylin and Eosin (H&E) staining showed that all defects treated with MSCs encapsulated in hydrogel were filled with soft tissues. However, bone and vessel formations were only observed in MSC laden MPEG-PCL-RGD group at 6 weeks ((C) of FIG. 22). This new bone formation and neovascularization were observed both at the edge and the center of the defects. In contrast, the defects in case of the negative-control and MSC-laden MPEG-PCL groups did not exhibit new bone formation ((A) and (B) of FIG. 22). The implanted hydrogels remained unabsorbed at the defects for all the groups, appearing as a granular form with MSCs. There were no inflammatory reactions in the implanted hydrogels. Masson's trichrome staining exhibited osteoid formation in MPEG-PCL-RGD-treated group at 6 weeks ((F) of FIG. 22). In MPEG-PCL-RGD group, mineralized bone and osteocytes surrounding the defected region were observed. New bone formation and fibrous-like tissue were hardly detectable in case of the negative control and MSC laden MPEG-PCL groups ((D) and (E) of FIG. 22). At 12 weeks, all experimental calvarial defects were almost completely regenerated (FIG. 23). These images showed the presence of abundant osteocytes in the lacunae, and mature bone formation was observed in the defected regions for all groups. Furthermore, Masson's thrichrome staining revealed that a large amount of collagenous tissue was generated in the defected regions for all groups.

In addition, the presence of cells within the defects was determined using GFP-MSC. At 6 weeks post implantation, GFP-MSCs were still located at the implanted site, and the signal of osteocalcin expression (red) was overlapped with that of GFP positive cells (green), indicating that the implanted cells were differentiated into osteoblast ((A) and (B) of FIG. 24). After 12 weeks, although GFP and osteocalcin positive cells were not disappeared in the MSC laden hydrogels, their signals were weakening ((C) and (D) of FIG. 24). These data indicated that the implanted MSCs could survive and differentiate into osteoblast in the calvarial defects.

Experimental Example 10. Calvarial Bone Regeneration Evaluated by CT and microCT Computed tomography (CT) (GE Brightspeed Elite Select 16ch MDCT, General Electric Medical System, USA) analysis was performed at the day 1, 6 weeks and 12 weeks after MSCs implantation. Formalin fixed samples were placed on the scanning platform of a microCT (SkyScan 1173, Kontich, Belgium). For all samples, 2D-projection images were reconstructed into 3D volumes. Volume of interest (VOI) was first selected for virtual extract and the volume of new bone was measured.

As a result, at the day 1, notable regeneration was not found in the defects of all groups. After 6 weeks post-implantation, the defects treated with MSCs laden MPEG-PCL-RGD were recovered with new bone. After 12 weeks post-implantation, these defects were substantially regenerated ((A) of FIG. 25). MicroCT data revealed new bone area and volume within the defects ((B) of FIG. 25). Two-dimensional sections (coronal and transverse planes) of microCT images demonstrated that the groups treated with MSCs encapsulated in hydrogel had marginal and central new bone formation in the defects at 6 weeks post-implantation. Particularly, MSC laden MPEG-PCL-RGD group showed great bone regeneration compare with MPEG-PCL group at 6 weeks post-implantation. In contrast, negative control group revealed only slight bone formation. The three dimensional construction images suggested that MPEG-PCL-RGD group showed significantly greater bone formation than negative-control and MPEG-PCL groups.

New bone formation was quantified with a bone volume (BV) in the defected regions ((C) of FIG. 25). The percentage of bone volume to total tissue volume (TV) was presented as a BV/TV ratio ((D) of FIG. 25). At 6 weeks, high levels of BV were observed in MPEG-PCL-RGD group ($2.84\pm1.33$ mm$^3$) compare with negative-control group ($0.59\pm0.14$ mm$^3$) and MPEG-PCL group ($1.34\pm1.34$ mm$^3$). Correspondingly, the BV/TV ratio revealed that MSCs encapsulated in MPEG-PCL-RGD hydrogel ($4.36\pm0.89\%$) were highly efficient in bone regeneration. Negative-control and MSCs laden MPEG-PCL group showed percentage healing of $0.84\pm0.3\%$ and $1.65\pm1.59\%$, respectively. At 12 weeks, no significant differences were observed in all experimental groups. These data indicated that the MSCs encapsulated in MPEG-PCL-RGD hydrogel had accelerated the bone regeneration.

INDUSTRIAL APPLICABILITY

The present invention relates to a thermosensitive biodegradable hydrogel. In this case, since the hydrogel according to the present invention includes methoxy polyethylene glycol-polycaprolactone (MPEG-PCL) to which a cell-adhesive peptide binds, and methoxy polyethylene glycol-polycaprolactone (MPEG-PCL), the hydrogel according to the present invention has excellent cellular adhesiveness while maintaining thermosensitivity of polymers intact, and can be biodegradable in vivo after a predetermined period of time, and thus can be effectively used in the field of tissue engineering.

What is claimed is:

1. A thermosensitive biodegradable hydrogel for tissue engineering support comprising a mixture of a methoxy polyethylene glycol-polycaprolactone (MPEG-PCL) copolymer, to which a cell-adhesive peptide binds, represented by the following Formula 1, and a methoxy polyethylene glycol-polycaprolactone (MPEG-PCL) copolymer represented by the following Formula 2:

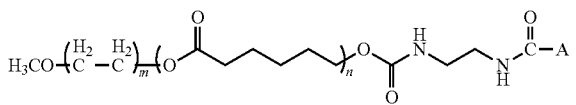

[Formula 1]

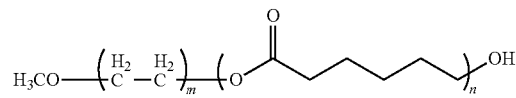

[Formula 2]

wherein m is in a range of 10 to 20, n is in a range of 15 to 30, and A represents a cell-adhesive peptide;

wherein the copolymer represented by Formula 1 is present at a content of 0.001 to 3% by weight or less, based on 100% by weight of the copolymer represented by Formula 2, and wherein the thermosensitive biodegradable hydrogel is present in a sol phase at room temperature and present in a gel phase at 30 to 37° C.

2. The thermosensitive biodegradable hydrogel of claim 1, wherein the cell-adhesive peptide comprises one or more selected from the group consisting of Arg-Gly-Asp (RGD), Arg-Glu-Asp-Val (REDV), Leu-Asp-Val (LDV), Tyr-Ile-Gly-Ser-Arg (YIGSR), Pro-Asp-Ser-Gly-Arg (PDSGR), Ile-Lys-Val-Ala-Val (IKVAV), and Arg-Asn-Ile-Ala-Glu-Ile-Ile-Lys-Asp-Ala (RNIAEIIKDA).

3. A method of preparing a thermosensitive biodegradable hydrogel for tissue engineering support, comprising:

mixing a methoxy polyethylene glycol-polycaprolactone (MPEG-PCL) copolymer, to which a cell-adhesive peptide binds, represented by the following Formula 1, and a methoxy polyethylene glycol-polycaprolactone (MPEG-PCL) copolymer represented by the following Formula 2:

[Formula 1]

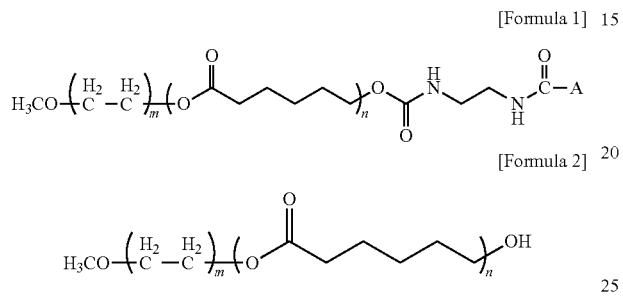

[Formula 2]

wherein m is in a range of 10 to 20, n is in a range of 15 to 30, and A represents a cell-adhesive peptide; and wherein the copolymer represented by Formula 1 is present at a content of 0.001 to 3% by weight or less, based on 100% by weight of the copolymer represented by Formula 2, and wherein the thermosensitive biodegradable hydrogel is present in a sol phase at room temperature and present in a gel phase at 30 to 37° C.

4. The method of claim 3, wherein the copolymer represented by Formula 1 is prepared through the following steps:

reacting the methoxy polyethylene glycol-polycaprolactone (MPEG-PCL) copolymer represented by Formula 2 with an imidazole compound;

reacting a diamine compound with the reaction product in the previous step; and reacting a cell-adhesive peptide with the reaction product in the previous step using a condensing agent.

5. The method of claim 4, wherein the condensing agent is 4-(4,6-dimethoxy-1,3,5-triazin-2-yl)-4-methyl morpholinium chloride (DMT-MM), or combination of 1-ethyl-3-(3-dimethylaminopropyl) carbodiimide (EDC) and N-hydroxysuccinimide (NHS).

* * * * *